United States Patent
Nelson et al.

[11] Patent Number: 5,875,976
[45] Date of Patent: Mar. 2, 1999

[54] LOCKING MECHANISM FOR NOZZLE ASSEMBLY

[75] Inventors: Sheldon Nelson, New Hope, Minn.; David Schiff, Highland Park, N.J.; Walter Stoeckmann, Mahopac, N.Y.

[73] Assignee: Medi-Ject Corporation, Minneapolis, Minn.

[21] Appl. No.: 773,659

[22] Filed: Dec. 24, 1996

[51] Int. Cl.[6] ............................. B05B 1/00; F16L 15/00
[52] U.S. Cl. ........................... 239/600; 239/71; 239/329; 239/331; 239/584; 285/92; 285/391; 285/401
[58] Field of Search ............................. 239/71, 320, 329, 239/331, 584, 600; 285/92, 391, 401, 402

[56] References Cited

U.S. PATENT DOCUMENTS

| | | | |
|---|---|---|---|
| D. 304,616 | 11/1989 | Dunlap et al. | D24/24 |
| D. 349,958 | 8/1994 | Hollis et al. | D24/112 |
| 620,821 | 3/1899 | Abbey et al. | 285/391 X |
| 1,311,145 | 7/1919 | Zeindler et al. | 285/391 X |
| 1,629,058 | 5/1927 | Wilson | 285/391 X |
| 1,645,032 | 10/1927 | Wilson | 285/391 X |
| 2,322,244 | 6/1943 | Lockhart | 123/215 |
| 2,322,245 | 6/1943 | Lockhart | 123/215 |
| 2,380,534 | 7/1945 | Lockhart | 128/215 |
| 2,390,246 | 12/1945 | Folkman | 128/215 |
| 2,398,544 | 4/1946 | Lockhart | 128/215 |
| 2,413,303 | 12/1946 | Folkman | 128/215 |
| 2,450,527 | 10/1948 | Smith et al. | 258/177 |
| 2,459,875 | 1/1949 | Folkman | 128/215 |
| 2,547,099 | 4/1951 | Smoot | 128/173 |
| 2,605,763 | 8/1952 | Smoot | 128/173 |
| 2,635,602 | 4/1953 | Hein, Jr. | 128/173 |
| 2,653,602 | 9/1953 | Smoot | 128/173 |
| 2,670,121 | 2/1954 | Scherer et al. | 128/272 |
| 2,671,347 | 3/1954 | Scherer | 74/2 |
| 2,681,653 | 6/1954 | Kuhne | 128/173 |
| 2,688,968 | 9/1954 | Scherer | 128/272 |
| 2,699,166 | 1/1955 | Dickinson, Jr. et al. | 128/173 |
| 2,704,542 | 3/1955 | Scherer | 128/173 |
| 2,704,543 | 3/1955 | Scherer | 128/173 |
| 2,705,953 | 4/1955 | Potez | 128/173 |
| 2,714,887 | 8/1955 | Venditty | 128/173 |
| 2,717,597 | 9/1955 | Hein, Jr. | 128/173 |
| 2,722,931 | 11/1955 | May | 128/173 |
| 2,737,946 | 3/1956 | Hein, Jr. | 128/173 |
| 2,754,818 | 7/1956 | Scherer | 128/173 |

(List continued on next page.)

FOREIGN PATENT DOCUMENTS

| | | | |
|---|---|---|---|
| 2028870 | 5/1991 | Canada | A61M 11/06 |
| 2071115 | 12/1992 | Canada | A61M 5/28 |
| 0 157 906 | 10/1985 | European Pat. Off. | A61M 25/00 |
| 0 460 961 | 12/1991 | European Pat. Off. | F41B 11/12 |
| 2 254 153 | 5/1974 | Germany | A61M 5/28 |
| 76202162 | 5/1986 | Taiwan . | |
| 959397 | 6/1964 | United Kingdom . | |
| 2 249 159 | 1/1994 | United Kingdom | F41B 11/00 |
| WO 95/03844 | 2/1995 | WIPO | A61M 5/30 |
| WO 96/15821 | 5/1996 | WIPO | A61M 5/30 |
| WO 96/19252 | 6/1996 | WIPO | A61M 5/30 |

OTHER PUBLICATIONS

Catalog: Hoechst Celanese—Advanced Materials Group, "Vectra® Liquid Crystal Polymer".
Catalog: Industrial Gas Springs, Ltd.

*Primary Examiner*—Andres Kashnikow
*Assistant Examiner*—Robin E. Evans
*Attorney, Agent, or Firm*—Pennie & Edmonds LLP

[57] ABSTRACT

The present invention is directed toward a locking mechanism for aiding in the prevention of accidental or unintentional disengagement of the nozzle assembly from a needleless injection device. In one embodiment of the locking mechanism, a stud positioned on the nozzle assembly engages a recess in the injector to help to deter the nozzle assembly from rotating during firing of the injector. In another embodiment of the locking mechanism, a nib on the nozzle assembly engages a recess in the injector to deter the nozzle assembly from rotating during firing of the injector. A retaining element may be utilized within the injector to provide the recesses for engagement with the locking mechanisms.

23 Claims, 9 Drawing Sheets

U.S. PATENT DOCUMENTS

| | | | |
|---|---|---|---|
| 2,762,369 | 9/1956 | Venditty | 128/173 |
| 2,762,370 | 9/1956 | Venditty | 128/173 |
| 2,764,977 | 10/1956 | Ferguson | 128/173 |
| 2,789,839 | 4/1957 | Siebert | 285/7 |
| 2,798,485 | 7/1957 | Hein, Jr. | 128/173 |
| 2,798,486 | 7/1957 | Hein, Jr. | 128/173 |
| 2,800,903 | 7/1957 | Smoot | 128/173 |
| 2,816,543 | 12/1957 | Venditty et al. | 128/173 |
| 2,816,544 | 12/1957 | Scherer et al. | 128/173 |
| 2,820,655 | 1/1958 | Hileman | 287/53 |
| 2,821,193 | 1/1958 | Ziherl et al. | 128/173 |
| 2,821,981 | 2/1958 | Ziherl et al. | 128/173 |
| 2,825,332 | 3/1958 | Johnson | 128/173 |
| 2,896,977 | 7/1959 | Hansen | 285/402 X |
| 2,902,994 | 9/1959 | Scherer | 128/173 |
| 2,921,582 | 1/1960 | Sadd | 128/173 |
| 2,928,390 | 3/1960 | Venditty et al. | 128/173 |
| 3,057,349 | 10/1962 | Ismach | 128/173 |
| 3,066,670 | 12/1962 | Stauffer | 128/218 |
| 3,115,133 | 12/1963 | Morando | 128/173 |
| 3,123,070 | 3/1964 | Kath | 128/173 |
| 3,129,708 | 4/1964 | Krantz | 128/173 |
| 3,130,723 | 4/1964 | Venditty et al. | 128/173 |
| 3,131,692 | 5/1964 | Love | 128/173 |
| 3,138,157 | 6/1964 | Ziherl et al. | 128/173 |
| 3,140,713 | 7/1964 | Ismach | 128/173 |
| 3,147,967 | 9/1964 | Bougeard | 267/65 |
| 3,167,071 | 1/1965 | Venditty | 128/173 |
| 3,189,029 | 6/1965 | Stephens | 128/173 |
| 3,202,151 | 8/1965 | Kath | 128/173 |
| 3,245,703 | 4/1966 | Manly | 285/319 |
| 3,292,622 | 12/1966 | Banker | 128/173 |
| 3,308,818 | 3/1967 | Rutkowski | 128/173 |
| 3,330,276 | 7/1967 | Gordon | 128/173 |
| 3,330,277 | 7/1967 | Gabriels | 128/173 |
| 3,335,722 | 8/1967 | Lowry et al. | 128/173 |
| 3,343,538 | 9/1967 | Morley | 128/215 |
| 3,343,798 | 9/1967 | Senft | 239/71 X |
| 3,353,537 | 11/1967 | Knox et al. | 128/218 |
| 3,399,759 | 9/1968 | Love | 206/1 |
| 3,406,684 | 10/1968 | Tsujino | 128/173 |
| 3,419,007 | 12/1968 | Love | 128/272 |
| 3,424,154 | 1/1969 | Kinsley | 128/173 |
| 3,425,413 | 2/1969 | Stephens | 128/173 |
| 3,442,536 | 5/1969 | Fowler | 285/391 X |
| 3,461,867 | 8/1969 | Zimmet et al. | 128/173 |
| 3,476,110 | 11/1969 | Yahner | 128/173 |
| 3,490,451 | 1/1970 | Yahner | 128/173 |
| 3,507,276 | 4/1970 | Burgess | 128/173 |
| 3,518,990 | 7/1970 | Banker | 128/173 |
| 3,521,633 | 7/1970 | Yahner | 128/173 |
| 3,526,225 | 9/1970 | Isobe | 128/173 |
| 3,527,212 | 9/1970 | Clark | 128/173 |
| 3,557,784 | 1/1971 | Shields | 128/173 |
| 3,561,443 | 2/1971 | Banker | 128/173 |
| 3,625,208 | 12/1971 | Frost et al. | 128/173 |
| 3,659,587 | 5/1972 | Baldwin | 128/2 |
| 3,688,765 | 9/1972 | Gasaway | 128/173 |
| 3,714,943 | 2/1973 | Yanof et al. | 128/173 |
| 3,768,472 | 10/1973 | Hodosh et al. | 128/218 |
| 3,779,371 | 12/1973 | Rovinski | 206/47 |
| 3,782,380 | 1/1974 | Van Der Gaast | 128/173 |
| 3,783,895 | 1/1974 | Weichselbaum | 137/588 |
| 3,788,315 | 1/1974 | Laurens | 128/173 |
| 3,805,783 | 4/1974 | Ismach | 128/173 |
| 3,827,601 | 8/1974 | Magrath et al. | 222/83 |
| 3,838,689 | 10/1974 | Cohen | 128/218 |
| 3,908,651 | 9/1975 | Fudge | 128/173 |
| 3,938,520 | 2/1976 | Scislowicz et al. | 128/272.3 |
| 3,945,379 | 3/1976 | Pritz et al. | 128/173 |
| 3,945,383 | 3/1976 | Bennett et al. | 128/272 |
| 4,026,212 | 5/1977 | Dardick | 102/39 |
| 4,059,107 | 11/1977 | Iriguchi et al. | 128/173 |
| 4,089,334 | 5/1978 | Schwwebel et al. | 128/173 |
| 4,141,675 | 2/1979 | O'Neill | 417/214 |
| 4,260,180 | 4/1981 | Halushka et al. | 285/391 X |
| 4,328,802 | 5/1982 | Curley et al. | 128/272.1 |
| 4,387,879 | 6/1983 | Tauschinski | 251/149.1 |
| 4,406,485 | 9/1983 | Giebeler | 285/92 |
| 4,421,508 | 12/1983 | Cohen | 604/70 |
| 4,447,225 | 5/1984 | Taff et al. | 604/71 |
| 4,500,075 | 2/1985 | Tsuchiya et al. | 267/8 |
| 4,505,709 | 3/1985 | Froning et al. | 604/411 |
| 4,507,113 | 3/1985 | Dunlap | 604/71 |
| 4,518,385 | 5/1985 | Lindmayer et al. | 604/68 |
| 4,561,856 | 12/1985 | Cochran | 604/143 |
| 4,588,403 | 5/1986 | Weiss et al. | 604/411 |
| 4,596,556 | 6/1986 | Morrow et al. | 604/70 |
| 4,616,856 | 10/1986 | Kowalyshen | 285/92 |
| 4,619,651 | 10/1986 | Kopfer et al. | 604/415 |
| 4,623,332 | 11/1986 | Lindmayer et al. | 604/68 |
| 4,626,242 | 12/1986 | Fejes et al. | 604/68 |
| 4,662,878 | 5/1987 | Lindmayer | 604/411 |
| 4,675,020 | 6/1987 | McPhee | 604/411 |
| 4,680,027 | 7/1987 | Parson et al. | 604/68 |
| 4,709,686 | 12/1987 | Taylor et al. | 124/67 |
| 4,722,728 | 2/1988 | Dixon | 604/68 |
| 4,744,786 | 5/1988 | Hooven | 604/143 |
| 4,768,568 | 9/1988 | Fournier et al. | 141/286 |
| 4,771,758 | 9/1988 | Taylor et al. | 124/68 |
| 4,775,173 | 10/1988 | Sauer | 285/174 |
| 4,790,824 | 12/1988 | Morrow et al. | 604/143 |
| 4,799,881 | 1/1989 | Grier et al. | 239/600 X |
| 4,834,149 | 5/1989 | Fournier et al. | 141/1 |
| 4,850,967 | 7/1989 | Cosmai | 604/68 |
| 4,863,427 | 9/1989 | Cocchi | 604/110 |
| 4,874,367 | 10/1989 | Edwards | 604/72 |
| 4,875,605 | 10/1989 | Weston | 222/402.24 |
| 4,883,483 | 11/1989 | Lindmayer | 604/411 |
| 4,909,488 | 3/1990 | Seibert et al. | 267/64.11 |
| 4,913,699 | 4/1990 | Parsons | 604/68 |
| 4,923,072 | 5/1990 | Rilliet | 215/247 |
| 4,940,460 | 7/1990 | Casey et al. | 604/143 |
| 4,941,880 | 7/1990 | Burns | 604/143 |
| 4,948,104 | 8/1990 | Wirges | 267/64.11 |
| 4,989,905 | 2/1991 | Rajecki | 285/319 |
| 5,024,656 | 6/1991 | Gasaway et al. | 604/70 |
| 5,031,266 | 7/1991 | Tillman et al. | 15/327.2 |
| 5,041,715 | 8/1991 | Muller | 219/721.64 |
| 5,052,725 | 10/1991 | Meyer et al. | 285/308 |
| 5,061,263 | 10/1991 | Yamazaki et al. | 604/403 |
| 5,062,830 | 11/1991 | Dunlap | 604/68 |
| 5,064,413 | 11/1991 | McKinnon et al. | 604/70 |
| 5,066,280 | 11/1991 | Braithwaite | 604/110 |
| 5,073,165 | 12/1991 | Edwards | 604/72 |
| 5,085,332 | 2/1992 | Gettig et al. | 215/249 |
| 5,116,313 | 5/1992 | McGregor | 604/70 |
| 5,135,507 | 8/1992 | Haber et al. | 604/187 |
| 5,141,157 | 8/1992 | Han et al. | 239/600 X |
| 5,161,786 | 11/1992 | Cohen | 267/64.12 |
| 5,165,560 | 11/1992 | Ennis, III et al. | 215/247 |
| 5,176,406 | 1/1993 | Straghan | 285/24 |
| 5,188,599 | 2/1993 | Botich et al. | 604/110 |
| 5,190,224 | 3/1993 | Hamilton | 239/600 |
| 5,190,523 | 3/1993 | Lindmayer | 604/72 |
| 5,193,517 | 3/1993 | Taylor et al. | 124/67 |
| 5,209,362 | 5/1993 | Lutzker | 215/225 |
| 5,224,932 | 7/1993 | Lappas | 604/80 |
| 5,226,882 | 7/1993 | Bates | 604/110 |
| 5,279,576 | 1/1994 | Loo et al. | 604/187 |
| 5,281,202 | 1/1994 | Weber et al. | 604/132 |
| 5,292,308 | 3/1994 | Ryan | 604/86 |

| | | | | | | |
|---|---|---|---|---|---|---|
| 5,304,128 | 4/1994 | Haber et al. .............................. 604/68 | | 5,399,163 | 3/1995 | Peterson et al. .......................... 604/68 |
| 5,312,335 | 5/1994 | McKinnon et al. ...................... 604/72 | | 5,407,431 | 4/1995 | Botich et al. ............................ 604/110 |
| 5,312,577 | 5/1994 | Peterson et al. ........................ 264/154 | | 5,413,471 | 5/1995 | Yamauchi ............................ 425/129.1 |
| 5,316,198 | 5/1994 | Fuchs et al. ............................. 222/321 | | 5,423,756 | 6/1995 | van der Merwe ...................... 605/110 |
| 5,334,144 | 8/1994 | Alchas et al. ............................. 604/68 | | 5,454,409 | 10/1995 | McAffer et al. ......................... 141/329 |
| 5,356,380 | 10/1994 | Hoekwater et al. ...................... 604/85 | | 5,480,381 | 1/1996 | Weston ...................................... 604/68 |
| 5,360,146 | 11/1994 | Ikushima ................................ 222/386 | | 5,499,972 | 3/1996 | Parsons ..................................... 604/68 |
| 5,383,851 | 1/1995 | McKinnon, Jr. et al. ................ 604/68 | | 5,569,189 | 10/1996 | Parsons ..................................... 604/68 |
| 5,397,196 | 3/1995 | Boiret et al. ........................ 285/401 X | | 5,599,302 | 2/1997 | Lilley et al. .............................. 604/68 |
| | | | | 5,643,211 | 7/1997 | Sadowski et al. ...................... 604/110 |

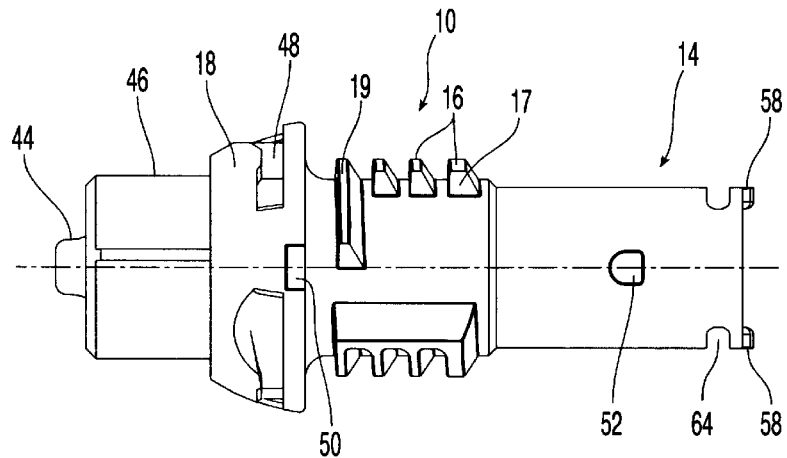
FIG. 4
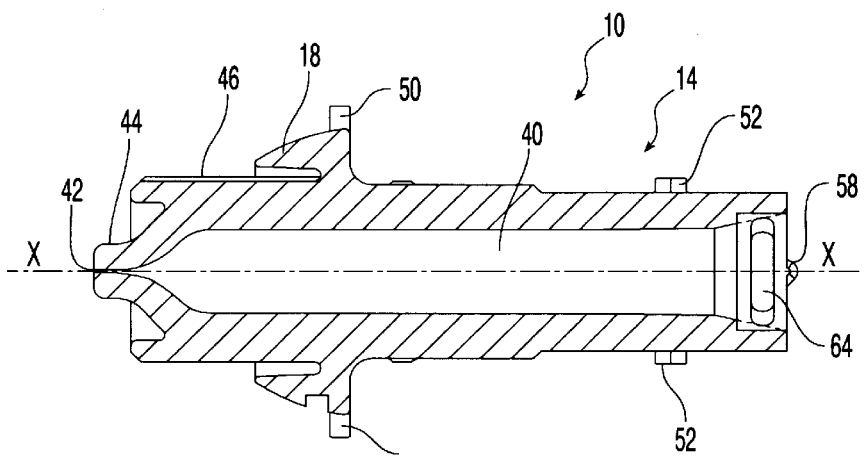
FIG. 5
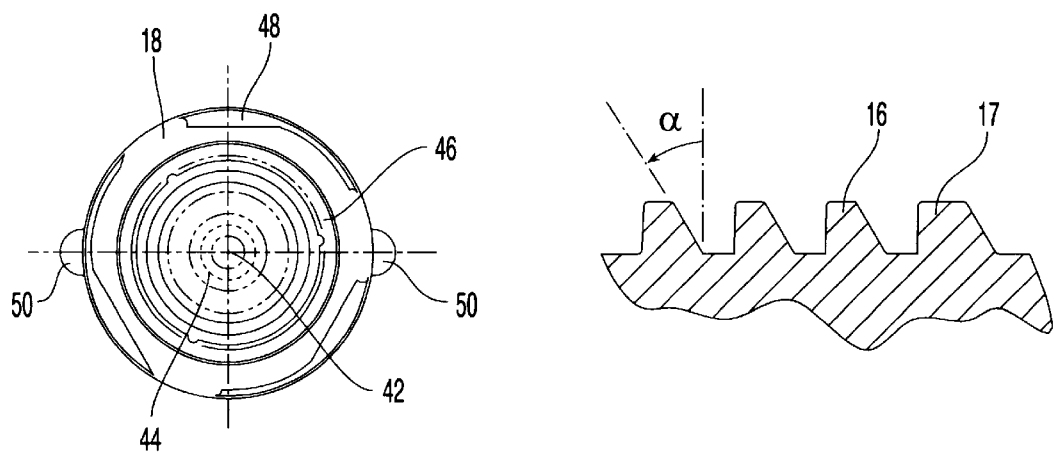
FIG. 6
FIG. 7

LOCKING MECHANISM FOR NOZZLE ASSEMBLY

FIELD OF THE INVENTION

The present invention generally relates to a nozzle assembly for a needleless fluid injection apparatus. More particularly, the present invention relates to a locking mechanism to aid in the prevention of accidental disengagement of the nozzle assembly from the injection apparatus and to a plunger for use in a nozzle assembly.

BACKGROUND OF THE INVENTION

Needleless hypodermic injection devices have been known and used in the past. These devices typically use spring or compressed gas driven plungers to accelerate a fluid at a velocity sufficient to pierce the skin and enter the underlying tissues.

Since at least the 1980s, the use of needleless injectors has become more desirable due to concerns over the spread of AIDS, hepatitis and other viral diseases caused by the possibility of accidental needle "sticks" from the conventional syringe and needle. Needleless injectors remove apprehensions of health care workers and are superior in eliminating accidental disease transmission.

A number of different needleless injectors are known including U.S. Pat. Nos. 5,062,830 to Dunlap, 4,790,824 to Morrow et al., 4,623,332 to Lindmayer et al., 4,421,508 to Cohen, 4,089,334 to Schwebel et al., 3,688,765 to Gasaway, 3,115,133 to Morando, 2,816,543 to Venditty, et al., and 2,754,818 to Scherer. These injectors typically include a nozzle assembly, which includes a medication holding chamber and a plunger. The chamber has an orifice through which a jet of medication is forced out of the chamber using the plunger actuated by a piston which is typically connected to some type of energy source.

Due to the high velocity of the jet and/or the high pressure of the energy source created by the typical needleless injector, it has been found that nozzle assemblies have a tendency to disengage during firing of the energy source. This can result in the creation of a dangerous situation, particularly if the nozzle assembly acts as a projectile. The tendency for this to occur has been found to be more pronounced with bayonet mounted nozzle assemblies, as shown in U.S. patent application Ser. No. 5,599,302 to Lilley et al. However, this problem may also exist with conventional screw-type mounts. Thus, there is a need for a locking mechanism which will deter the nozzle assembly from unexpectedly releasing from the injector body.

Nozzle assemblies for injectors typically include a plunger installed inside of the internal chamber of the nozzle assembly for moving the medicament from the nozzle assembly. After expelling the medicament, it is desirable to remove the nozzle assembly from the injector for either sterilization or disposal.

A problem associated with nozzle assemblies is the tendency for the plunger to remain attached to the piston of the injector after the energy source has fired. Thus, when either a disposable or reusable nozzle assembly is removed from the injection apparatus, the plunger may remain connected to the piston. In order to avoid possible contamination, the plunger must be removed from the injector for either disposal or re-sterilization. It is often difficult to remove these plungers and sometimes necessary to destroy them in the process of removing them. It is, therefore, desirable to provide a plunger which will allow easy removal from the injection apparatus and which may be removable with the nozzle assembly.

SUMMARY OF THE INVENTION

Accordingly, the present invention relates to a nozzle assembly for use with an injector. The nozzle assembly includes a tubular body with a tip end, a tail end, and an internal chamber defined between the two ends. The tip end is for positioning against an injection site. The tail end is for connecting to an injector. The internal chamber holds medicament and includes an orifice at the tip end for expelling the medicament out of the chamber. The nozzle assembly also includes a connecting means such as threads or teeth. The connecting means are disposed around the circumference of the tubular body and are used to engage the nozzle assembly with the injector. The nozzle assembly also includes a means for locking the tubular body into the injector. This locking means includes at least one recess in the injector, and at least one protrusion position on an external surface of the tubular body. The protrusion is configured to engage the recess.

The connecting means may be centrally located on the tubular body and the protrusion may be positioned between the connecting means and the tail end of the nozzle assembly.

The connecting means may be teeth which are partially surrounding the circumference of the body in the form of rib segments. The injector may include grooves for mating with the teeth of the nozzle assembly. The teeth may also be in the form of a partial helix, surrounding a partial circumference of the tubular body.

The nozzle assembly may also include a retaining element having the recess for engagement by the protrusion. The retaining element has a first end for accepting the nozzle assembly, and a second end opposite the first end forming a wall with an opening. The retaining element is a cylindrical ring with an internal diameter at least equal to or greater than the external diameter of the nozzle assembly tubular body. The retaining element is retained within the interior of the injector.

The recess may be an L-shaped slot having a first and second elongated opening for accepting the protrusion of the nozzle assembly. The first opening of the L-shaped slot may extend axially from the first end of the retaining element, partially along the length of the retaining element. The second opening of the L-shaped slot may extend helically and partially around the circumference of the retaining element from the first opening. The second opening includes a detent for receiving the protrusion. The detent is preferably sized so that the user receives positive tactile feedback when the protrusion enters the detent. When the protrusion enters the detent, the tubular body is in a locked position. The second opening is at an angle which is substantially equal to the helical angle of the teeth of the connecting means so that when the nozzle assembly is inserted into and turned in the retaining element, the protrusion travels axially at the same rate as the teeth.

The protrusion may extend longitudinally from the tail end of the tubular body. When the protrusion extends longitudinally, the recess in the injector may be located in the wall of the retaining element. The protrusion may be sized so that the user receives positive tactile feedback when the protrusion enters the recess. A slot may be positioned in the tubular body adjacent the protrusion extending partially transversely at the tail end of the nozzle assembly. This slot allows for depression of the protrusion as the nozzle assembly is rotated before the protrusion enters the recess. When the protrusion is positioned in the recess, the tubular body is in a locked position.

The present invention also relates to an indicating means for aligning the tubular body locking means with the injector, both prior to insertion and after the tubular body has been rotated into a final position. The indicating means indicates to the user that the nozzle assembly is properly aligned with the injector.

The indicating means may include a first and third marking which are positioned on the tubular body. A second marking may be positioned on the exterior of the injector. The first marking aligns with the second marking when the tubular body is inserted longitudinally into the injector. The third marking aligns with the second marking after the tubular body has been inserted longitudinally and rotated into a locked position.

The present invention also relates to a nozzle assembly with a tubular body and a connecting means. The connecting means is disposed around the circumference of the tubular body for engaging with the injector. The connecting means includes a plurality of teeth which at least partially surround the circumference of the tubular body to define rib segments. At least one of the rib segments is configured differently than the other rib segments for insuring proper positioning of the nozzle assembly in the injector.

The differently configured rib segment may have a wider cross-section than the other rib segments. A groove is provided in the injector which is configured and dimensioned for receiving the wider rib segment. The differently configured rib segment may be longer than the other rib segments. A portion of the injector is configured and dimensioned to interfere with the longer rib segment to deter improper insertion of the nozzle assembly into the injector.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
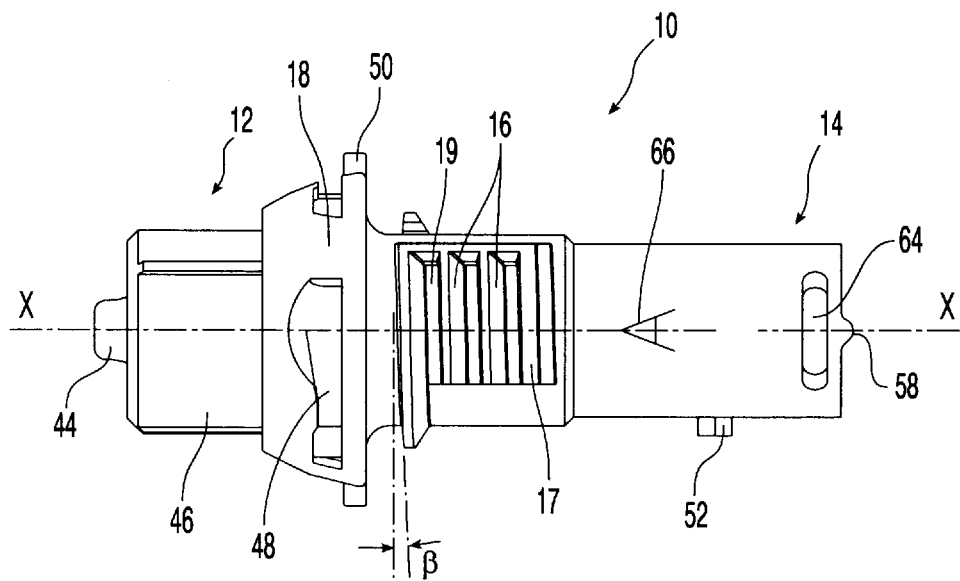
FIG. 1 is an elevated side view of an injector nozzle incorporating the locking features of the present invention.
Figure 2:
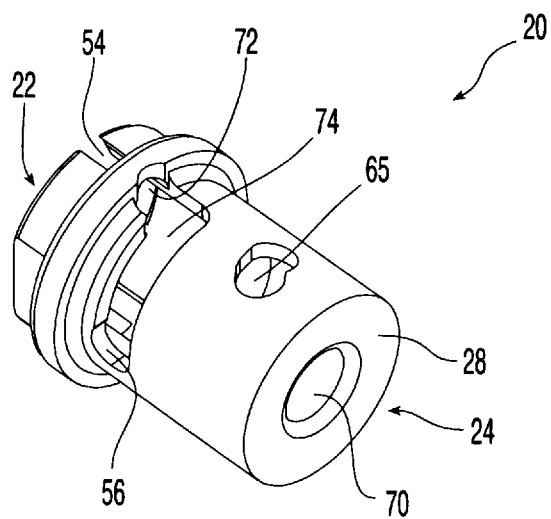
FIG. 2 is a perspective view of a retaining element for use with an injector nozzle which incorporates the locking feature of the present invention.

The exterior of a nozzle assembly 10 is shown in FIG. 1 with several embodiments of the locking mechanism of the present invention installed thereon. A retaining element 20, or retaining ring, is shown in FIG. 2. The present invention utilizes a nozzle assembly 10 incorporating a locking mechanism in conjunction with a retaining element 20 in an injector 30. This combination will deter unexpected disengagement of the nozzle assembly 10 from the injector 30.

Figure 3:
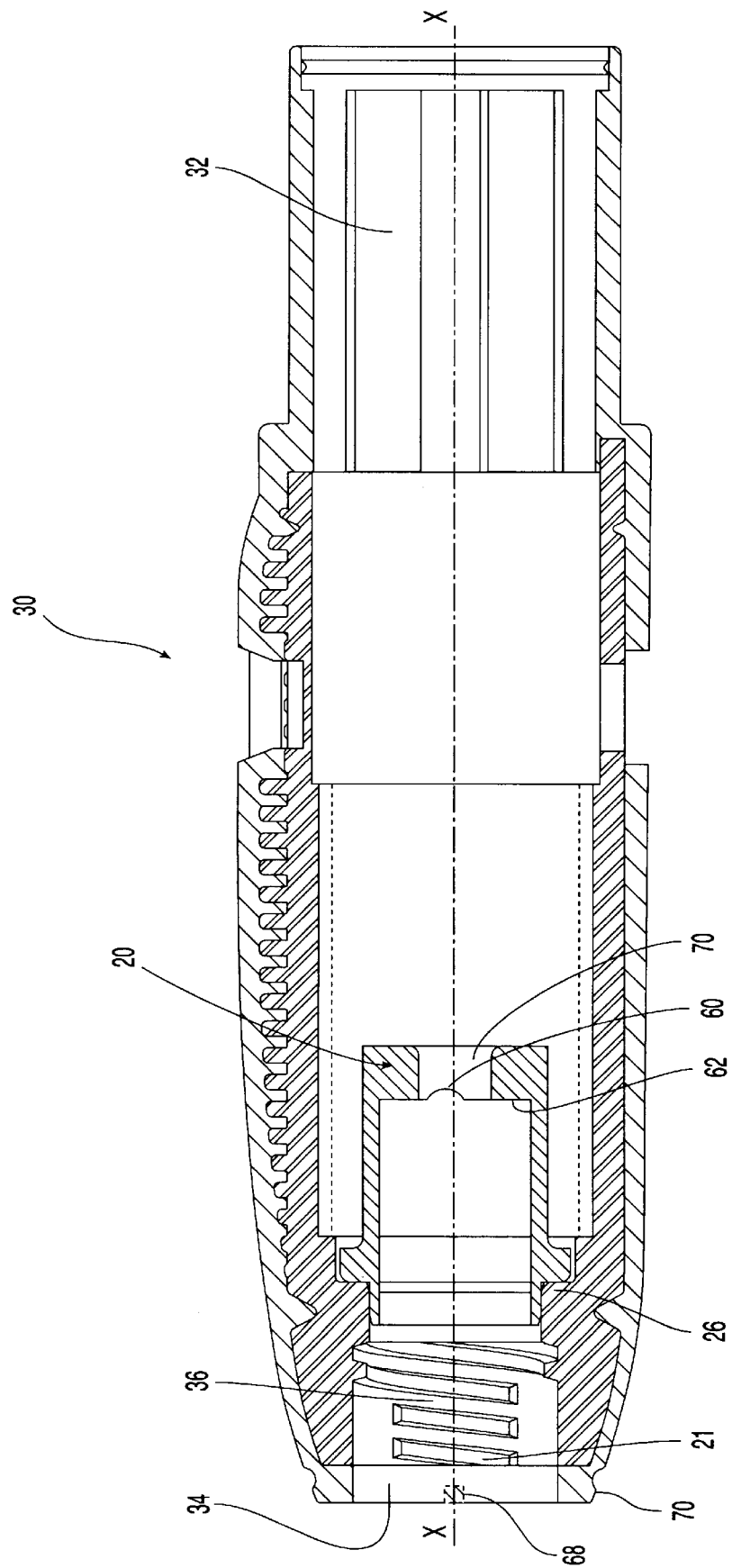
FIG. 3 is a cross-sectional side view of an injector body including a retaining element for receiving a nozzle incorporating the locking features of the present invention.

An injector 30 is shown in FIG. 3 with the retaining element 20 disposed inside of injector 30 near the distal end thereof. The nozzle assembly 10 is typically installed in a distal end of injector 30. The injector 30 is shown for illustration purposes only since the present invention is not intended to teach one of ordinary skill in the art how to make an injector. For this purpose, U.S. patent application Ser. No. 5,599,302 to Lilley et al. may be utilized for an injector with a gas spring energy source, the contents of which is incorporated herein by reference. It should be noted that any type of injector may be utilized with the locking mechanism of the present invention. Further, any type of energy source may be utilized with the present invention, such as a gas spring, coil spring, or compressed gas. Also, the nozzle assemblies contemplated for use with this invention may be either disposable or reusable.

As used in this application, the terms distal or front shall designate the end or direction toward the nozzle assembly 10 of the injector 30. The terms proximal or rear shall designate the end or direction toward the power unit 32. The term longitudinal designates an axis X—X connecting nozzle assembly 10 to power unit 32, and the term transverse designates a direction substantially perpendicular to the longitudinal direction including arcs along the surface of injector 30.

Referring again to FIG. 1, a nozzle assembly of the present invention is depicted. Nozzle assembly 10 has a tubular body and includes a tip 12 at the distal end and a tail 14 at the proximal end. The nozzle assembly 10 also includes a plurality of threads 16 disposed on the body of the nozzle assembly 10 between the tip 12 and tail 14 and a transition portion 18 located between the threads 16 and the tip 12.

The threads 16 are preferably in a partial helix pattern around the circumference of the nozzle assembly tubular body 10. Threads 16, when in the partial helix pattern, form rib segments 16. The rib segments 16 are preferably canted at an angle β which preferably ranges from about 0° to 7° with a range of 0° to 3° being most preferred, as shown in FIG. 1. Angle β is measured from a plane drawn perpendicular to the longitudinal axis X—X of nozzle assembly 10. Rib segments 16 are spaced apart relative to each other and are preferably at a predetermined pitch. Pitch determines the rate of axial travel of the nozzle assembly when the rib segments are rotated by defining the spacing between the rib segments 16. Pitch is preferably about 0.08 inches per thread, but can vary over a range of about 0.04 to 0.2 inches per thread. It has been found that the nozzle assembly is more likely to disengage or unscrew when pitch and angle β is larger, such as at a 7° angle and a 0.1 inches per thread pitch. Thus, a larger β and pitch results in a greater likelihood of disengagement.

The tail 14 is for insertion into a distal end 34 of an injector 30. When the tail 14 is inserted into the injector body 30, the rib segments 16 are received by corresponding grooves 36 in the interior of the injector 30 so that the rib segments 16 and tail 14 of the nozzle assembly 10 are housed within the injector after insertion and rotation. When the ribs have been inserted and rotated properly, they are then in their final position.

The rib segments 16, as shown in FIG. 1, are of the bayonet mount type. Conventional screw type threads may also be used. When the tail 14 and rib segments 16 are inserted into the injector 30, the nozzle assembly 10 is rotated in order to engage the bayonet mount rib segments 16 with the grooves 36 in the interior of the injector 30. The transition portion 18, being of a larger diameter than the rib segments 16 and tail 14, then rests at the distal end of the injector 30.

Figure 4:
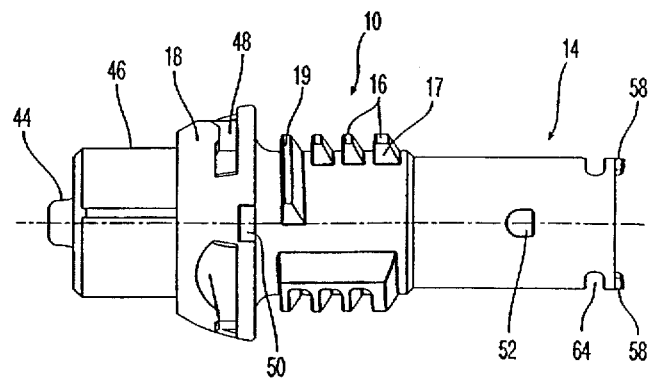
FIG. 4 is an elevated top view of an injector nozzle incorporating the locking features of the present invention.
Figure 7:
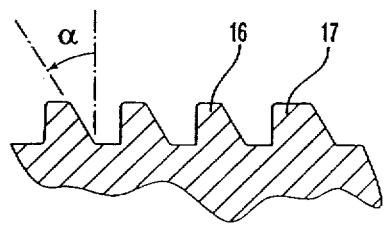
FIG. 7 is an exploded cross-sectional view of the bayonet mounts of the nozzle assembly.
Figure 8:
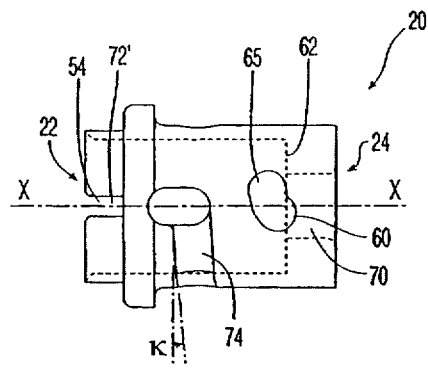
Figure 9:
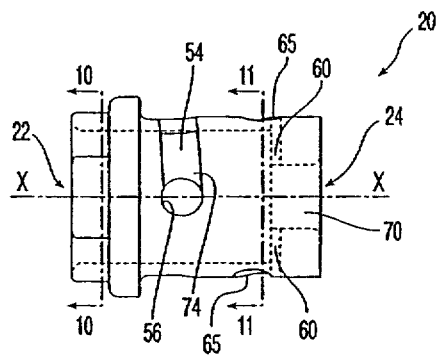
Figure 10:
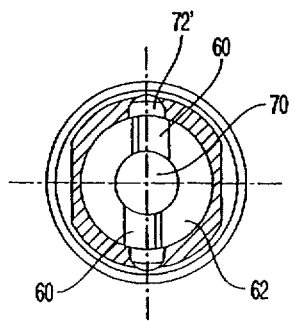
Figure 11:
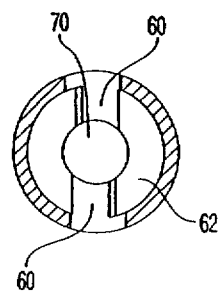
Figure 16:
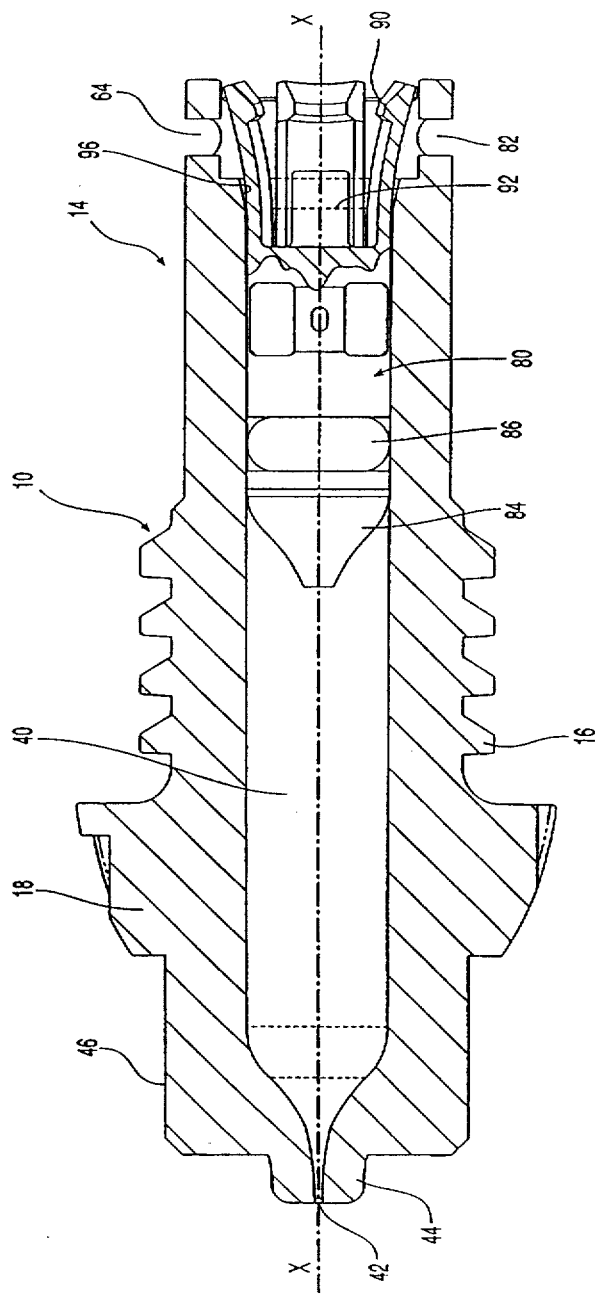

Referring to FIGS. 1, 4, and 7, the preferred rib segments 16 for connecting to the injector 30 are of the quarter turn variety, meaning they are positioned about substantially ¼ of the circumference of the body on one side and about ¼ of the circumference of the body on the opposite side. It is preferred that the lead or proximal-most thread 17 be wider in cross-section than the other threads. It is also preferred that the remaining rib segments 16 be of the same cross-sectional width, although this is not required. Tooth 17 is wider than the remaining teeth in order to insure that nozzle assembly 10 is fully inserted into the injector 30 prior to being rotated into locked position. Since the grooves 36 in injector 30 are preferably sized to receive rib segments 16, the proximal-most groove for receiving rib segments 16 is preferably wider than the other grooves. Thus, unless the nozzle assembly 10 is fully inserted into injector 30, it is difficult, if not impossible, to rotate the nozzle assembly 10 into a locked position.

In addition, the distal-most thread 19 is preferably a half-thread. By half-thread it is meant that the thread 19 is positioned about substantially ½ the circumference of the nozzle assembly 10. This thread 19 interferes with the distal-most ridge 21 associated with grooves 36. Since grooves 36 are preferably disposed on opposite internal sides of injector 30, the half thread 19 is not able to pass by ridge 21. In this manner, nozzle assembly 10 is deterred from being inserted too far into the distal end of injector 30. The combination of wide tooth 17 and long tooth 19 helps to insure the nozzle assembly 10 is properly positioned into injector 30 prior to firing.

Further, as shown in FIG. 7, it has been found that the cross-sectional dimension of rib segments 16 is important, although not critical, to the present invention. The preferred type of teeth 16 for the bayonet mount are typically referred to as buttress threads. These threads are preferred where the threads are required to receive a large longitudinal load. Buttress-type threads also help to deter the rib segments 16 from twisting when under load. As shown in FIG. 7, the buttress threads 16 preferably have a distal edge which is preferably substantially perpendicular to the longitudinal axis X—X (FIG. 5), a flat top which is substantially parallel to the longitudinal axis X—X, and an angled proximal edge. The slope of distal edge is preferably within about 10° of the perpendicular. The angled proximal edge is preferably 29°, as measured from the plane of the flat top surface, but can preferably vary over a range of about 20° to 40°.

Figure 5:
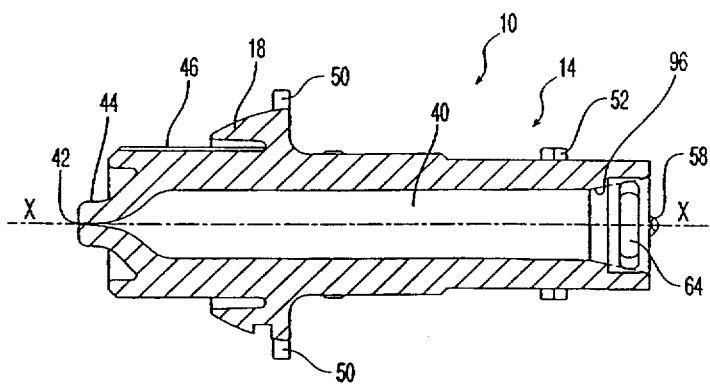
FIG. 5 is a cross-sectional side view of the injector nozzle shown in FIG. 1.

As depicted in FIGS. 1, 4, and 5, nozzle assembly 10 has an elongated body defining a chamber 40 which communicates with an orifice 42 at the distal end of the nozzle assembly 10. Fluid such as liquid medicament can pass into the chamber 40 through orifice 42. Also fluid can pass out of the orifice 42 during the injection process. The body of the nozzle assembly 10 is generally cylindrical and, at its distal end, has a conical tip 44 with the orifice 42 positioned centrally in the tip 44 preferably along the longitudinal axis X—X of nozzle assembly 10. A cylindrical collar 46 extends proximally from the rear end of conical tip 44. Following the collar 46 in the proximal direction is the transition portion 18, which may be utilized to connect the nozzle assembly 10 to an adapter (not shown), a cap (not shown), or any other device which is desirable to attach to the tip end of a nozzle assembly. Transition portion 18 preferably includes a plurality of depressions 48 which are configured and dimensioned for engaging with another device, of the type discussed above. The transition portion 18 also preferably includes an indicating tab 50 which extends outwardly on either side of the transition portion 18. Indicating tab 50 will be discussed more fully below.

The depressions 48 on the transition portion 18 may be of any type which will allow connection of the nozzle assembly 10 to another device. Following the transition portion 18 in the proximal direction are the rib segments 16 which are followed by the tail portion 14. The tail portion 14 includes the locking mechanisms of the present invention.

It has been found that, because of the high velocity jet created when the injector 30 is fired, the nozzle assembly 10 has a tendency to disengage by unscrewing during firing. This effect is more pronounced when bayonet mounts, as shown in FIGS. 1 and 4, are used, but can also be found to exist where conventional screw type mounts are used. It is desirable to have a mechanism for inhibiting or locking the injector in order to avoid unintentional or accidental disengagement of the nozzle assembly. The present invention is directed to several mechanisms for locking the nozzle assembly in place during firing.

A first embodiment of the locking mechanism is found in the use of a stud 52 which protrudes from the external circumference of the tail portion 14 of the nozzle assembly 10. Two studs 52, as shown in FIG. 5, are preferred, although a single stud 52 may be used effectively. The two studs are preferably positioned on opposite sides of the tail 14. When the tail 14 is inserted into the injector 30, the stud 52 engages in a recess 54 in the interior of the injector 30. This recess 54 may be provided by the retaining element 20, as will be discussed in greater detail below.

It is preferred that, when the tail 14 and rib segments 16 are inserted into the injector 30 and rotated to turn the rib segments 16 into the grooves 36, the stud 52 is allowed to travel in the recess 54 until it reaches a final locked position 56. The stud 52 preferably travels axially at the same rate as the rib segments 16. When the stud 52 has traveled to the final locked position 56, the nozzle assembly 10 has been entirely screwed into the injector 30. As the stud 52 reaches the final locked position, the user preferably receives positive feedback that the nozzle assembly 10 has been locked in. This positive feedback may be a clicking noise or tactile feedback. Upon reaching the locked position, the user also preferably realizes a decrease in resistance, thereby knowing that they have reached the correct and final locked position 56.

A second embodiment of the locking mechanism is found in the use of nibs or protrusions 58 which extend proximally and longitudinally from the tail 14 of the nozzle assembly 10. While two nibs 58 are preferred, one may be used effectively. The nibs 58 are preferably positioned on opposite sides of the tail 14, as shown in FIG. 4. Most preferably, the nibs 58 are positioned at 0° and 180° while the studs 52 are positioned at 90° and 270°. When the tail 14 is inserted into the injector 30, the nibs 58 engage in recesses 60 in the interior of the injector 30. The recesses 60 may be provided in the retaining element 20 which is disposed within the injector 30 interior.

It is preferred that, when the tail 14 and rib segments 16 are inserted into the injector 30 and rotated to turn the rib segments 16 into the grooves 36, the nibs 58 are slightly depressible and travel along an internal surface of the injector 30 until they engage the recess 60.

A transverse slot 64 is preferably positioned adjacent the nibs 58. This slot 64 allows the nibs 58 to exhibit deformable characteristics. If plastic or a similar softer material is utilized for the nozzle assembly body, it is possible to use the nib 58 without the slot 64. However, in order to allow the nibs 58 to flex inwardly, it is desirable to provide the slots 64 next to the nibs in order to allow the nibs 58 to flex slightly inwardly until they reach the recess 60. The nibs 58 reach the final locked position when they enter the recess 60. When the nibs 58 reach the recess 60, the nozzle assembly 10 has been entirely screwed into the injector 30. As the nibs 58 reach the final locked position 60, the user preferably receives positive feedback that the nozzle assembly 10 has been locked in. This positive feedback may be a clicking noise or tactile feedback. Upon reaching the locked position, the user also preferably realizes a decrease in resistance, thereby knowing that the correct and final locked position has been reached. The nibs 58 are preferably rounded, which aids in their travel within the injector 30 prior to reaching the final locked position.

Both the nibs 58 and studs 52 exhibit sufficient deformable characteristics to allow the nozzle assembly 10 to be unscrewed from the injector 30.

According to a preferred embodiment of the present invention, the nozzle assembly 10 discussed above is formed integrally of metal and preferably stainless steel. This type of nozzle assembly 10 is generally reusable. Another preferred embodiment of the nozzle assembly 10 is formed integrally of plastic. This type of nozzle assembly 10 is generally disposable. Other materials can also be used to construct the nozzle assembly 10. A preferred plastic is a polycarbonate such as Makrolon, manufactured by Bayer.

Another feature of the present invention is the use of indicating means for properly positioning the nozzle assembly 10 in the injector 30. The nozzle assembly 10 may preferably include two different indicators 50, 66, although it is anticipated that one indicator can be used without the other. The injector 30 should preferably also include another indicator 68 which is used in conjunction with the indicators 50, 66 on the nozzle assembly 10 to properly align the nozzle assembly 10. The indicator 68 on the injector 30 is located along the rim 70 of the injector 30 at the distal end. This indicator 68 may be an outwardly extending tab or protrusion, but is preferably a marking, such as a darkened line or square, as shown in FIG. 3 in phantom. The indicator 68 on the injector 30 works in conjunction with the indicators 50, 66 on the nozzle assembly 10. These indicators 50, 66, 68 are useful because nozzle assemblies are routinely removed from the body of the injector 30. By providing indicators, the nozzle assembly 10 can be easily aligned for proper insertion into the injector.

There are two types of indicators provided on the nozzle assembly 10. The first indicator 66 may be disposed on one side of the circumference of the tail section 14 or preferably on two sides. This indicator may be etched into the nozzle assembly tail 14 or molded into the tail 14 as a raised indicator 66. The indicator 66 shown in FIG. 1 is in the form of an "A", but may be any other type of indicating marking such as a dot.

Figure 6:
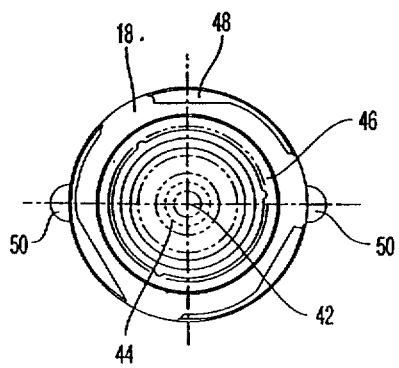
FIG. 6 is an end view of the tip of the injector nozzle showing the indicating tabs on either side.

The second indicator 50, as discussed above, is preferably located on the transition portion 18 and is disposed at the proximal edge of the transition portion 18. This indicator 50 preferably extends outwardly from the transition portion 18. As shown in FIG. 6, two second indicators 50 are preferred, although one may be used. The second indicator 50 is preferably a tab which extends outwardly from the side of the transition portion 18.

The first indicators 66 are preferably positioned at the same rotational angle as the nibs 58 and the second indicators 50 are preferably positioned at the same rotational angle as the studs 52. Thus, the first indicators 66 are preferably positioned at 0° and 180° and the second indicators 50 are positioned at 90° and 270°. However, the spacing of the indicators is determined by the difference in position between the engagement or entry point of the nozzle assembly into the injector and the locking point. Thus, the indicating means can be used independently of a locking means, such as the stud and recess. For instance, an indicating means could be used to show the user how to insert a nozzle assembly having bayonet mount teeth into the injector and, after rotation of the nozzle assembly, can be used to indicate that the nozzle assembly has been fully rotated.

In operation, the first indicator 66 is preferably aligned with the injector indicator 68 and the nozzle assembly 10 is inserted into the injector 30. Then the nozzle assembly 10 is rotated in order to engage the rib segments 16 with the grooves 36 and the locking mechanisms 52, 58 with the recesses 54, 60. When the nozzle assembly 10 has been entirely screwed in such that the locking mechanisms 52, 58 engage the recesses 54, 60, the second indicators 50 will align with the injector indicators 68 to indicate to the user that the nozzle assembly 10 has been properly installed on the injector 30.

As discussed above, a retaining element 20 may be used in the injector 30 to work in conjunction with the locking mechanisms 52, 58. A retaining element 20 is desirable because it can be made of a metal, such as stainless steel, while the injector 30 may be made of a softer material such as plastic. A metal retaining element provides the locking mechanisms with a strong surface against which they abut. As such, this provides better protection from unexpected disengagement. A metal retaining element is less likely to fail than a conventional plastic injector body. The metal retaining element is also useful because it can be readily inserted into an injector 30 with a limited amount of modification to the injector 30. The retaining element 20 is shown in perspective in FIG. 2. and in elevated views in FIGS. 8 and 9.

The retaining element 20 is preferably a cylindrical body having a distal end 22 and a proximal end 24. As shown in FIG. 3, the retaining element 20 is preferably secured near the distal end of the injector body. The retaining element 20 may be secured within the injector 30 by positioning it behind an annular ridge 26 within the interior of the injector 30. The power unit 32 is then located proximally from the retaining element 20. The nozzle assembly tail 14 may be inserted into the distal end 22 of the retaining element 20. Therefore, the retaining element 20 is preferably sized to accept the tail portion 14 of the nozzle assembly 10.

Figure 10:
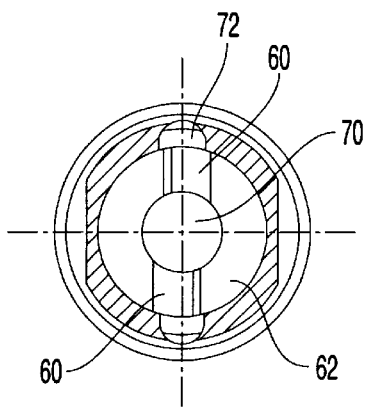
FIG. 10 is a cross-sectional view of the retaining element taken along plane 10—10 as shown in FIG. 8.
Figure 11:
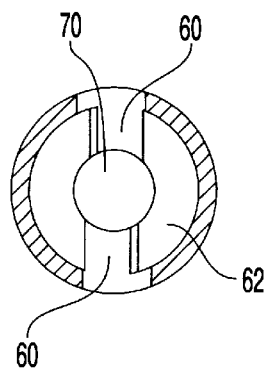
FIG. 11 is a cross-sectional view of the retaining element taken along plane 11—11 as shown in FIG. 8.

A wall 28 is preferably located at the proximal end 24 of the retaining element 20. The wall 28 preferably includes an opening 70 for receiving the piston 72 (shown in FIGS. 14 and 15) of the injector 30, as shown in FIGS. 10 and 11. The piston 72 accepts energy from the power unit 32 to drive the medicament out of the internal chamber 40 of nozzle assembly 10. Thus, the opening 70 in wall 28 is sized to accept the diameter of the piston 72.

Figure 8:
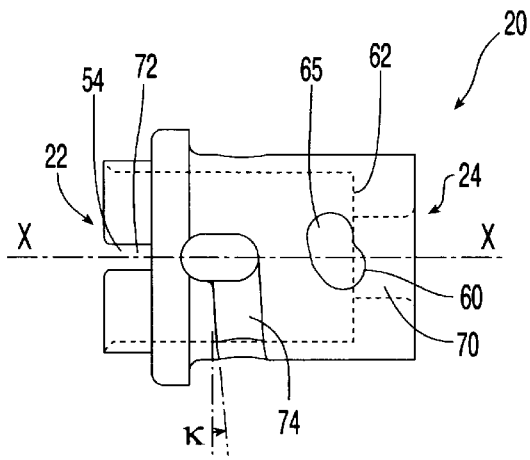
FIG. 8 is an elevated top view of the retaining element of the present invention shown in FIG. 2.
Figure 9:
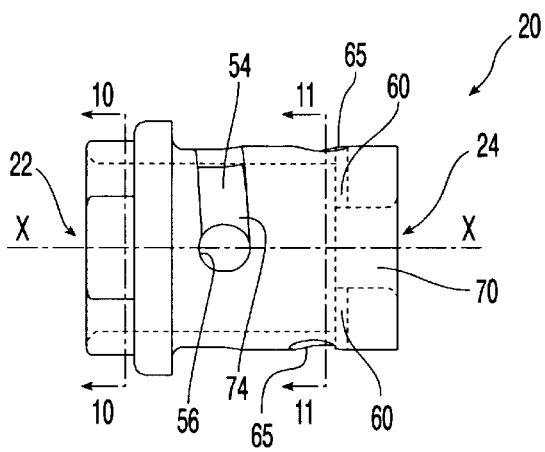
FIG. 9 is an elevated side view of the retaining element shown in FIG. 2.

The wall 28 also includes at least one recess or groove 60 for accepting the second locking mechanism, the nib 58. As shown in FIGS. 10 and 11, the grooves 60 runs perpendicular to the longitudinal axis X—X of the retaining element 20 in wall 28. As shown in FIGS. 2, 8 and 9, retaining element 20 includes apertures 65 to facilitate matching of grooves 60. The grooves extend from the outer circumference of the retaining element 20 to the opening 70 in the wall 28. When two nibs 58 are used on the nozzle assembly 10, the grooves 60 are preferably asymmetrical or radially offset from the center line of opening 70. The grooves 60 are asymmetrical to provide a sharp drop off for entry of the nib 58 into the groove 60. The grooves 60 are preferably rotated 180° relative to each other on wall 28 to accommodate nibs 58, which are also preferably rotated 180° relative to each other. However, if nibs 58 are not positioned at 180° relative to each other, grooves 60 will preferably be at the same radial angles as nibs 58.

The retaining element 20 also includes a recess 54 for receiving the first locking mechanism, the stud 52. This second recess 54 is preferably in the shape of a substantially L-shaped slot. A first opening 72 of the slot extends axially from the distal end of the retaining element 20 partially along the length of the retaining element 20. A second opening 74 of the slot 54 extends from the end of the first slot at an angle K in a helix pattern. This angle K is preferably the same pitch and angle β as the partial helix of the rib segments 16 of the nozzle assembly 10. The angle K allows stud 52 to travel axially at the same rate as the rib segments 16. A detent 56 is located at the other end of the second opening 74 for receiving the stud 52 in the locked position.

In use, when both the stud 52 and nibs 58 are utilized on the nozzle assembly 10, the nozzle assembly 10 is inserted into the injector 30 and retaining element 20 such that the stud 52 aligns with the first opening 72 of the L-shaped slot 54. When the nozzle assembly 10 has been fully inserted longitudinally into the retaining element 20, it is rotated in order to rotate the rib segments 16 of the bayonet into the corresponding grooves 36 in the injector 30, as shown in FIG. 3. The second opening 74 of slot 54 is preferably dimensioned such that a light interference fit occurs between the nozzle assembly 10 and retaining element 20 as the rib segments 16 are rotated into grooves 36. As the nozzle assembly 10 is rotated, the stud 52 travels along the second opening 74 of the L-shaped slot 54 until it enters the detent 56. When the stud 52 enters the detent 56, the nozzle assembly 10 should be fully rotated so that the rib segments 16 and grooves 36 have engaged. When the stud 52 reaches the detent 56, the user preferably encounters a clicking noise or a tactile sensation signalling to the user that the stud 52 has entered the detent 56. This tactile sensation will be one of reduced resistance. Once the stud 52 is located in the detent 56, the first locking mechanism 52 is engaged and will deter the nozzle assembly 10 from disengaging during firing of the injector 30. In addition to providing a locked position, the L-shaped slot helps to insure that the nozzle assembly is properly inserted and positioned in the injector. Thus, the L-shaped slot also helps to deter improper engagement of the nozzle assembly in the injector.

As for the second locking mechanism 58, when the nozzle assembly 10 is rotated in the retaining element 20 to engage the rib segments 16 with the grooves 36 in the injector 30, the nibs 58 encounter resistance against the inner side of wall 28. As the rib segments 16 are turned further, this resistance increases. When the slot 64 is provided in the tail 14 of the nozzle assembly 10 adjacent the nibs 58, the nibs will deform slightly inwardly enough to allow the nozzle assembly 10 to be fully rotated into the retaining element 20 and injector 30. As the rib segments 16 reach the end of their travel path within the grooves 36, the nibs 58 will enter the recess 60 disposed in the inner side of the wall 28 so that when the nozzle assembly 10 is fully rotated into the final position, the nibs 58 will be located in the recesses 60. This locking mechanism helps to deter the nozzle assembly 10 from disengaging unexpectedly during firing because the nozzle assembly 10 is deterred from rotating. The combination of the two locking mechanism 52, 58 used simultaneously, helps to further ensure that the nozzle assembly 10 will not disengage. This combined with the use of optimized pitch bayonet threads 16 will further help to deter unexpected disengagement.

Figure 12:
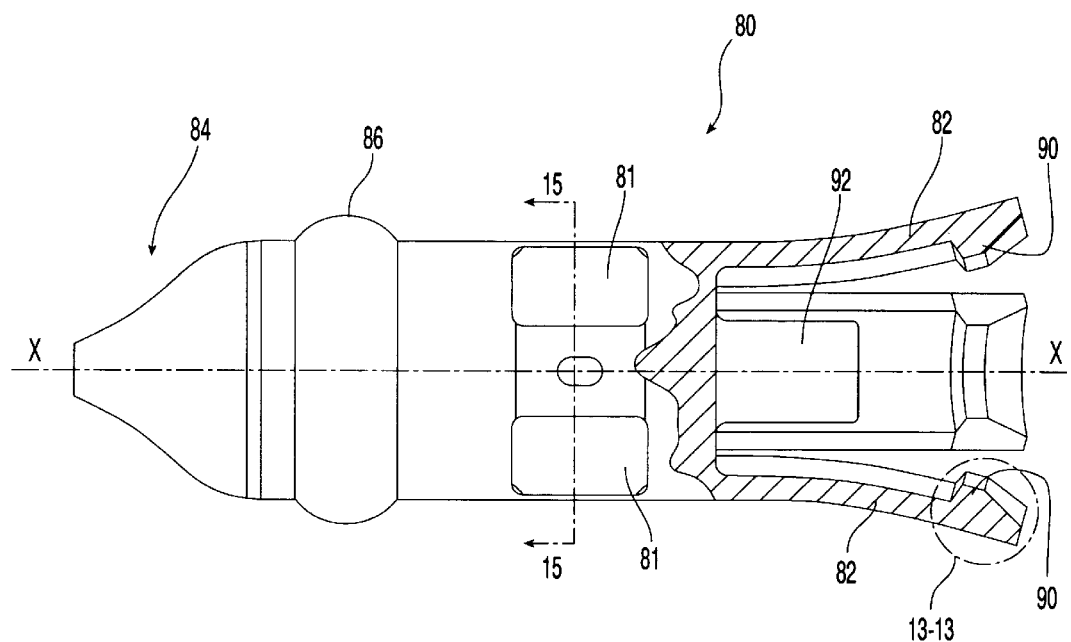
FIG. 12 is a partial cross-sectional view of one embodiment the plunger of the present invention.
Figure 16:
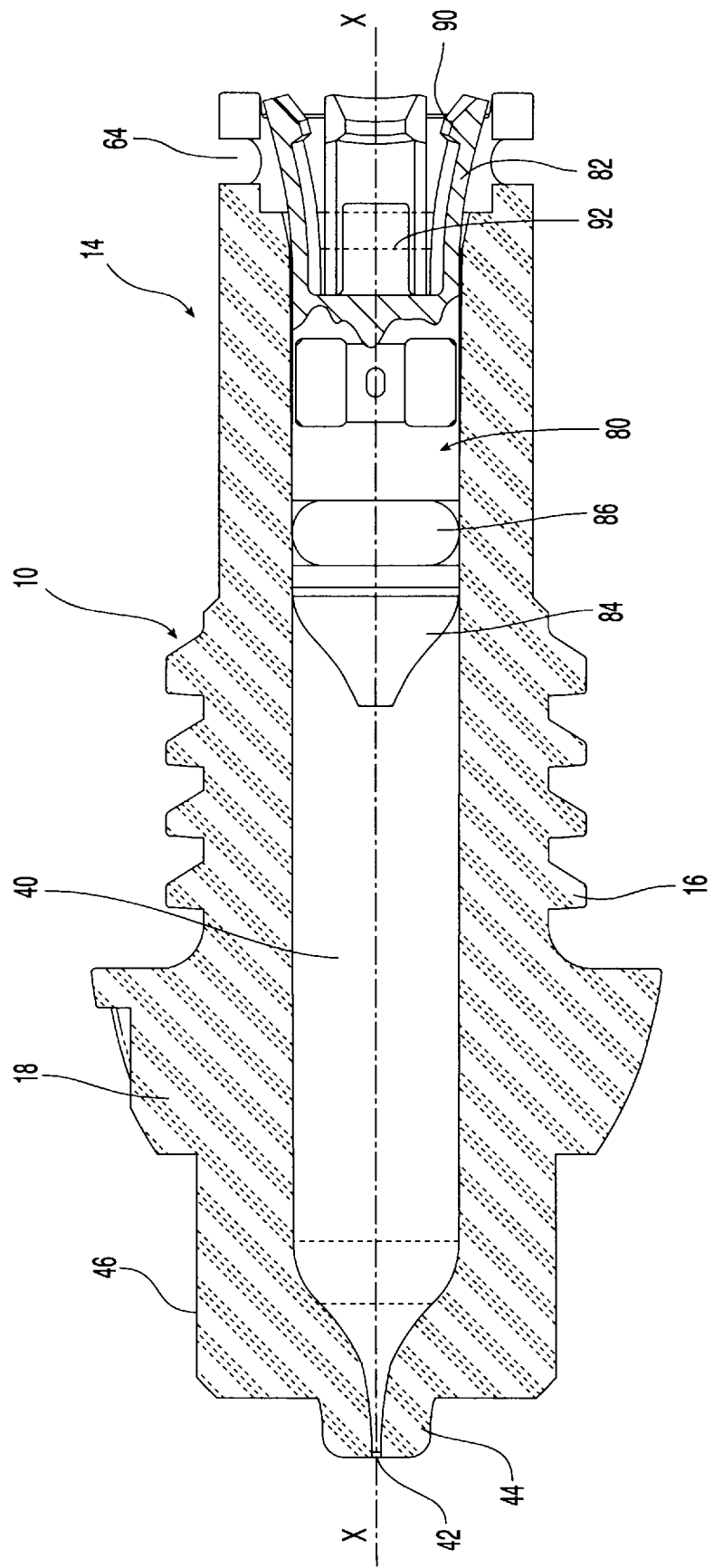
FIG. 16 is a cross-sectional view of the plunger installed in the internal chamber of the nozzle assembly after the injector has been fired and the piston of the injector has been withdrawn.

FIG. 12 shows a first embodiment of the improved plunger design of the present invention. The plunger 80 is typically situated in the internal chamber 40 of the nozzle assembly 10, as shown in FIG. 16. As shown more clearly in FIG. 21 for a second embodiment of plunger 80, when the nozzle assembly 10 is attached to the injector 30, the plunger 80 becomes attached to the piston 72 of the injector 30. The piston 72 is connected to the power source 32 so that when the power source 32 is fired, the piston 72 moves the plunger 80 distally to expel medicament from the internal chamber 40 through orifice 42.

After the injector 30 has been fired, the plunger 80 moves to the distal end of the chamber 40. In order to recharge the power source and to replace the nozzle assembly 10, the plunger 80 must be removed from the piston 72 so that a sterile nozzle assembly may be reinstalled. A problem has been found with prior plungers in that they were often difficult to remove from the piston 72 after firing so that when the nozzle assembly was removed from the injector 30, the plunger 80 remained attached to the piston. As a result, the plungers needed to be manually removed, such as by force or by destruction. The present plunger 80 and nozzle assembly 10 designed alleviates this problem by providing outwardly curved prongs or legs 82 on the plunger 80.

As shown in FIG. 12, the plunger 80 of the present invention includes a distal end and a proximal end. The plunger 80 is preferably cylindrical in shape and is sized to fit snugly, but slideably within the internal chamber 40 of the nozzle assembly 10. The tip 84 of the plunger 80 is located at the distal end and is preferably shaped to substantially match the internal contours of the internal chamber 40 of the nozzle assembly 10 at its distal end. The plunger 80 preferably includes a seal 86 adjacent the tip 84. The seal 86 helps to prevent any medicament from passing by the seal 86 before or during firing of the injector 30. The seal 86 is preferably compressed during use in order to provide a tight fit within the internal chamber 40, as shown in FIG. 16.

Figure 14:
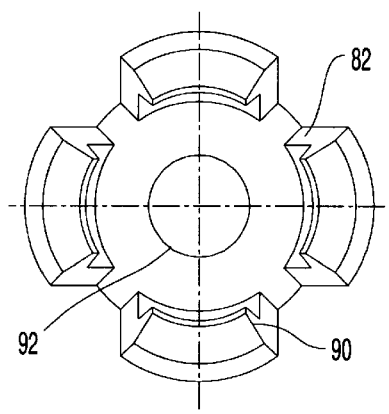
FIG. 14 is a proximal end view of the plunger shown in FIG. 12.
Figure 21:
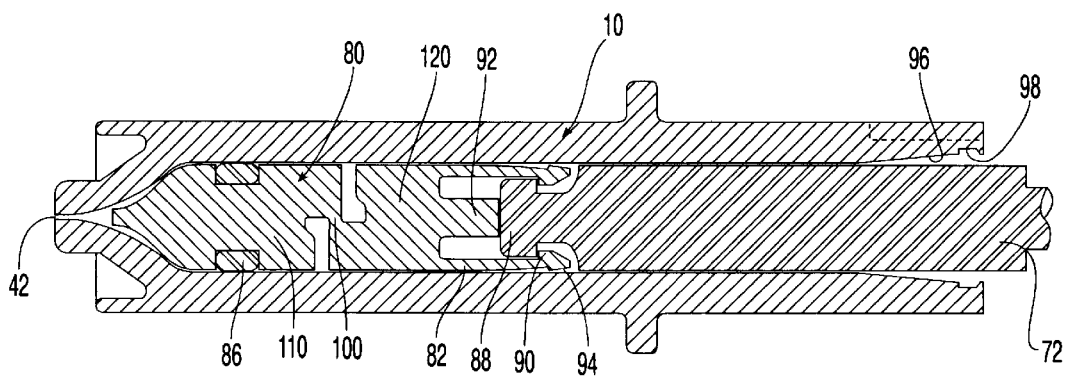
FIG. 21 is a cross-sectional view of the plunger of FIG. 17 installed in the internal chamber of the nozzle assembly prior to loading the chamber with medicament.

A plurality of prongs or legs 82 are located at the proximal end of the plunger 80. The prongs 82 are for attaching to piston or ram 72 of injector 30. The prongs 82 of the present invention are normally outwardly curved or flexed, but are flexible enough to be bend against their normal position so that the plunger 80 may slide within chamber 40. As shown in FIG. 14, four prongs 82 are preferred, although any number of prongs 82 may be used. A lead portion 88 of piston 72 is preferably shaped to connect with the plunger prongs 82, as shown in FIG. 21. Each prong 82 includes a lip 90 for encircling the lead portion 88 of the piston 72. Each prong 82 is preferably spaced at even angles around the outer circumference of the plunger 80. The plunger 80 also includes a post 92 which is positioned along the longitudinal axis X—X of the plunger 80 centrally between the prongs 82. This post 92 is for contact with the piston 72 when the power source 32 is fired. When the power source 32 is fired, the piston 72 moves distally until it contacts the post 92, at which point the plunger 80 and piston 72 move together to expel medicament from the internal chamber 40 through the orifice 42. If the lead portion of the piston 72 is substantially the same length as the distance between the prong lips 90 and the post 92, the piston 72 will not move longitudinally relative to the plunger 80. If the lead portion 88 of the piston 72 is smaller than the length of the distance between the lips 90 and the post 92, the piston 72 will move longitudinally relative to the plunger 80 until it contacts the post 92.

Figure 13:
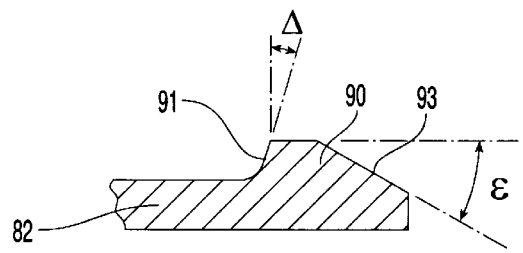
FIG. 13 is a cross-sectional view of one of the prongs on the plunger of FIG. 12.

The outwardly curved prongs 82 of the plunger 80 may be shorter in length than the length of the plunger 80 and extend at the proximal end thereof. Lip 90 is located at the proximal end of the prongs 82, as shown in exploded cross-sectional view in FIG. 13. The proximal end of prong 82 preferably includes several sloped surfaces. A first sloped surface 91 is preferably at an angle Δ of about 20°, but may range from about 0° to 40°. This sloped surface aids the plunger in disengaging from the piston 72. A second sloped surface 93 is preferably at an angle E of about 30°, but may range from about 0° to 90°. The second sloped surface is provided to aid lead portion 88 in entering the proximal end of plunger 80 to engage with prongs 82 when a nozzle assembly 10 is inserted into an injector 30.

Figure 15:
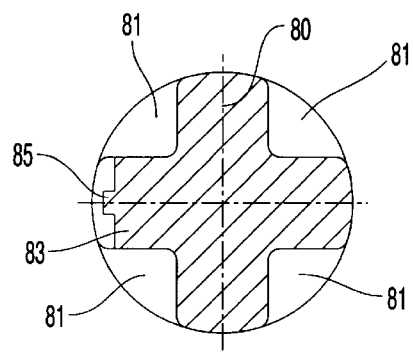
FIG. 15 is a cross-sectional view of the plunger at area 15—15 as shown in FIG. 12.

FIG. 15 shows a cross-section of plunger 80 at area 15—15. At this location, plunger 80 is cylindrical and preferably exhibits a circular cross-section with recesses 81 to form an X or cross shape. At one side, the cross-shaped section has a shortened arm 83 with an outwardly extending protrusion 85. Since plunger 80 is typically manufactured by molding, recesses 81 and shortened arm 83 are utilized in the molding process. Recesses 81 are cored out in order to reduce shrinkage of the plunger. Arm 83 is utilized as a connection point to the mold and protrusion 85 is a point at which the plunger is released from the mold. By providing shortened arm 83, no additional surface finishing of the plunger is required after separation from the mold.

The nozzle assembly 10 internal chamber 40 includes a tapered portion 96 at the proximal end for receiving the outwardly curved prongs 82, as shown in FIGS. 5 and 16. This tapered portion 96 is preferably sufficiently tapered to allow the prongs 82 of the plunger 80 to enter the taper and allow the piston 72 to be released from the plunger 80 after firing.

In operation, the plunger 80 rests within internal chamber 40 such that prongs 82 are compressed inwardly against their outwardly curved characteristic. After the injector 30 is fired, the plunger 80 is located at the distal end of the internal chamber 40. In order to rearm the power source 32 and to replace the nozzle assembly 10 for the next injection, the piston 72 is withdrawn proximally. As the piston 72 is moved proximally and as the plunger 80 reaches the outwardly flared portion 96 of the internal chamber 40, as shown in FIG. 16, the outwardly curved prongs 82 curve outwardly to assume their relaxed position and enter the tapered portion 96. Since the prongs 82 are allowed to bend outwardly to their relaxed position, clearance is provided so that the lips 90 of prongs 82 no longer engage with the lead portion 88 of the piston 72. As a result, the piston 72 is easily withdrawn from the plunger prongs 82. When the nozzle assembly 10 is unscrewed from the injector 30, the plunger 80 remains within the nozzle assembly 10, thereby alleviating the problem which previously existed with the plunger 80 failing to release from the piston 72.

The plunger 80 of the first embodiment is preferably constructed of a plastic material, although other materials may be used. Plastic is typically selected where the plunger is disposable. Preferred plastic materials include the following polymers: polycarbonate, acrylic, polypropylene and polystyrene.

Figure 17:
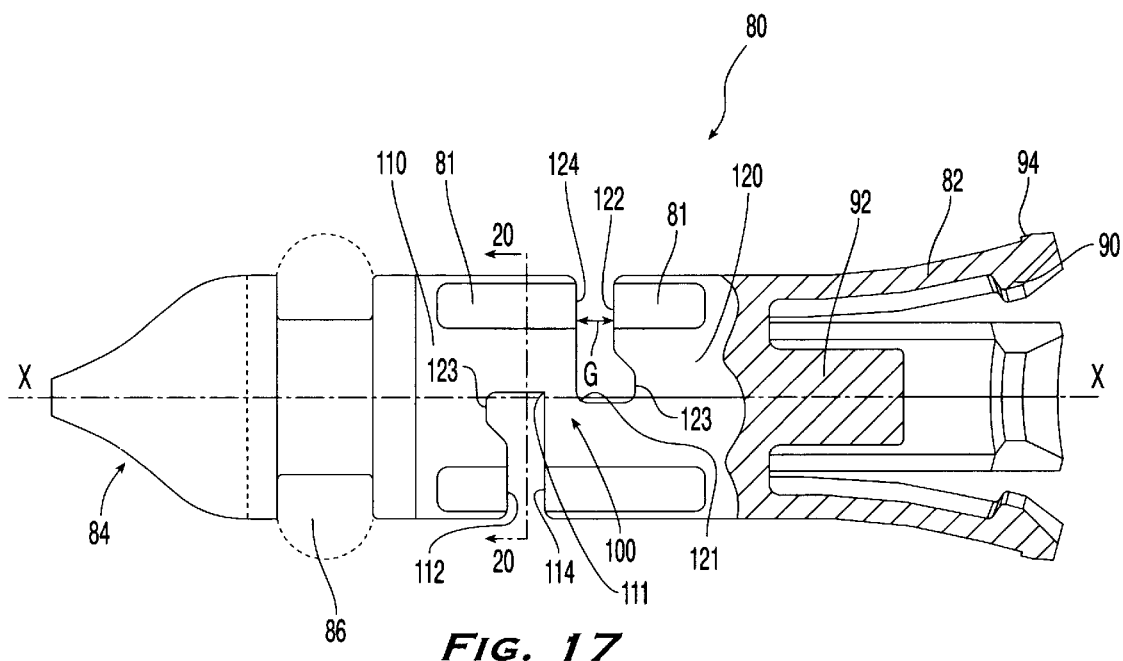
FIG. 17 is a partial cross-sectional view of another embodiment of the plunger of the present invention.

A second embodiment of plunger 80 is shown in FIG. 17. This plunger 80 exhibits many of the same features as the plunger shown in FIG. 12, but also includes a frangible portion 100. The plunger 80 includes a distal end and a proximal end and is preferably cylindrical in shape and sized to fit snugly, but slideably within the internal chamber 40 of the nozzle assembly 10. The tip 84 of the plunger 80 is located at the distal end and is preferably shaped to substantially match the internal contours of the internal chamber 40 of the nozzle assembly 10 at its distal end. The plunger 80 preferably includes a seal 86 adjacent the tip 84. The seal 86 helps to prevent any medicament from passing by the seal 86 before or during firing of the injector 30. The seal 86 is preferably compressed during use in order to provide a tight fit within the internal chamber 40, as shown in FIG. 16.

Figure 18:
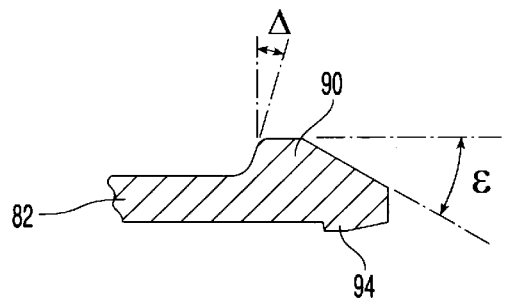
FIG. 18 is a cross-sectional view of one of the prongs on the plunger of FIG. 17.
Figure 19:
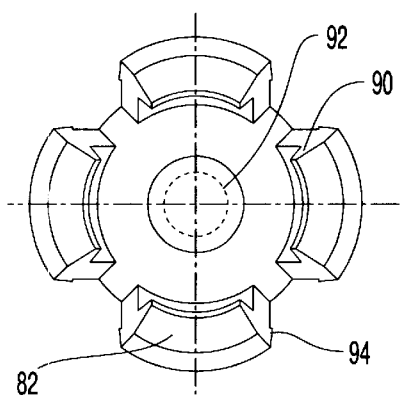
FIG. 19 is a proximal end view of the plunger shown in FIG. 17.

The plurality of prongs or legs 82 are located at the proximal end of the plunger 80. The prongs 82 are normally outwardly curved. A lead portion 88 of piston 72 is preferably shaped to connect with the plunger prongs 82 as shown in FIG. 21. Each prong 82 includes a lip 90 for encircling their lead portion 88 of the piston 72. In addition to including a lip 90 on their inner surface, prongs 82 include a ridge 94 on the external surface. Both the lip 90 and the ridge 94 are located at the proximal end of prongs 82, as shown in exploded cross-sectional view in FIG. 18.

Figure 22A:
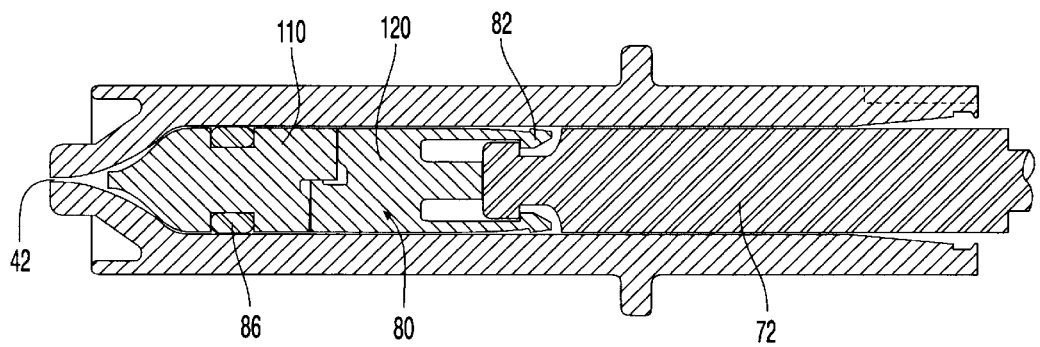
FIG. 22A is a cross-sectional view of the plunger of FIG. 17 installed in the internal chamber of the nozzle assembly after the injector has been fired.
Figure 22B:
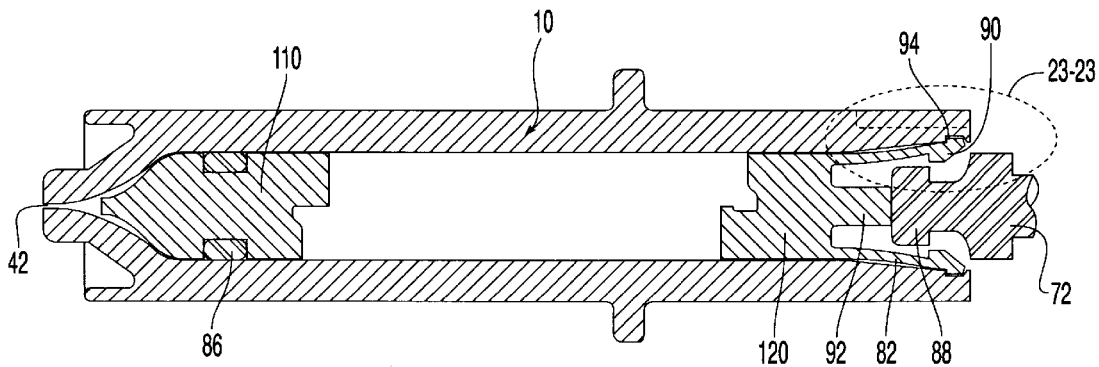
FIG. 22B is a cross-sectional view of the plunger of FIG. 17 installed in the internal chamber of the nozzle assembly after the injector has been fired, the nozzle assembly has been rotated out of locked position and the piston of the injector is about to be withdrawn.
Figure 23:
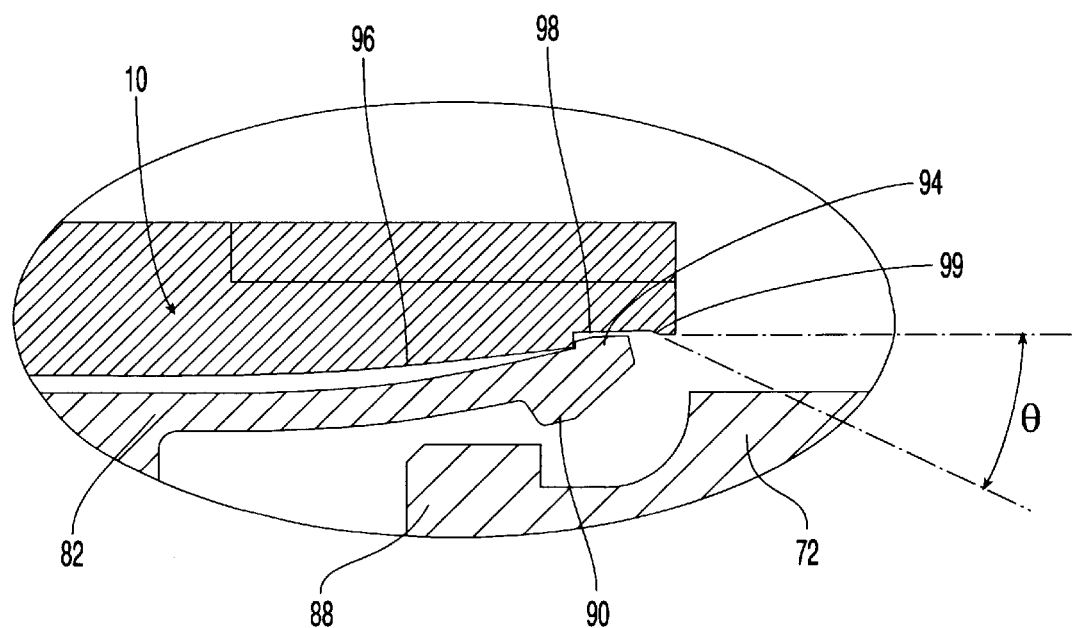
FIG. 23 is an exploded view of area 23—23 from FIG. 22 of the proximal end of one of the legs of the plunger in mating arrangement with the internal chamber of the nozzle assembly as the piston of the injector is being withdrawn.
Figure 1:
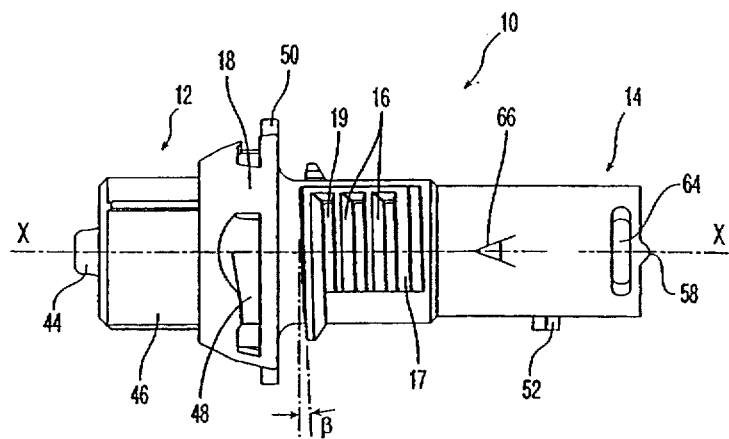
Figure 2:
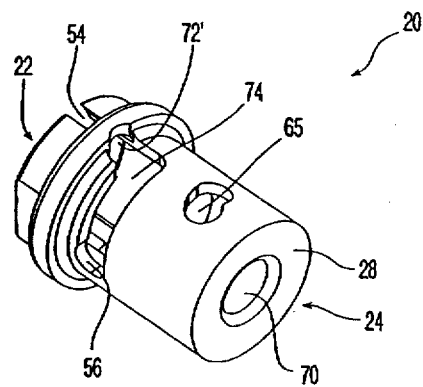
Figure 3:
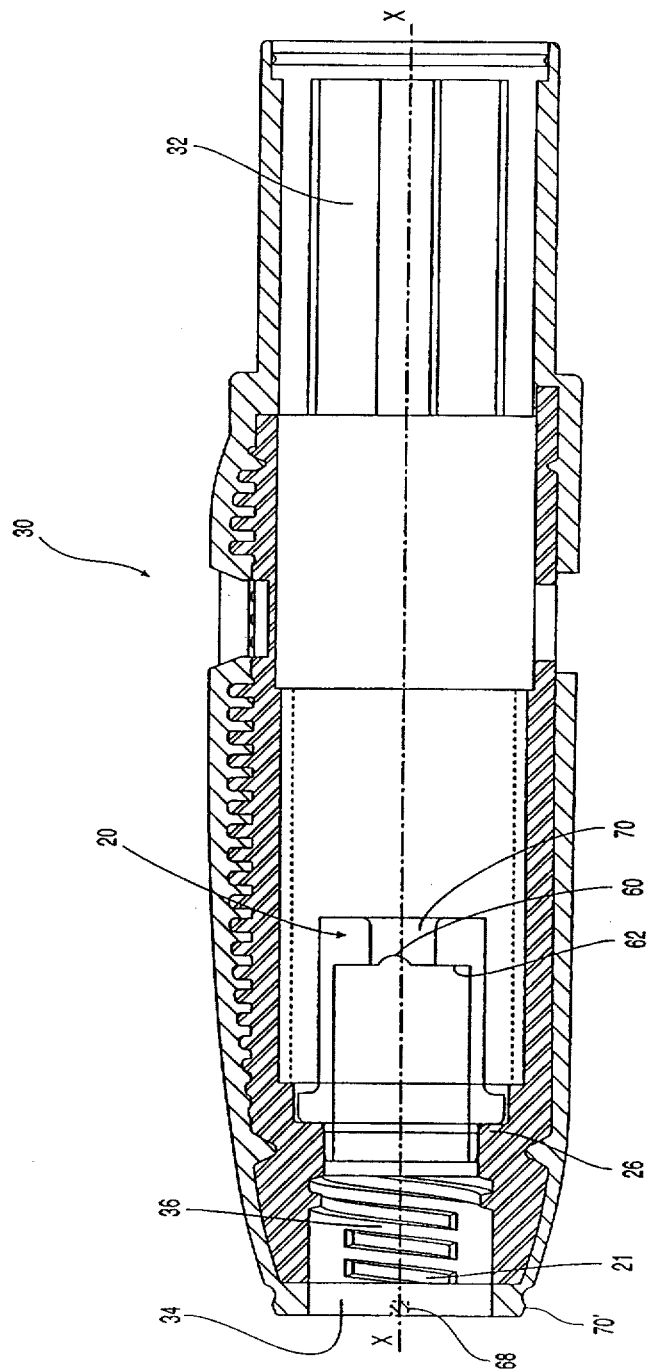

Ridge 94 is for associating with an annular groove 98 in tapered portion 96 at the proximal end of the nozzle assembly 10, as shown in FIGS. 21–23. Groove 98 is preferably located near the widest portion of outwardly tapered portion 96 and is sized to receive ridge 94. This groove 98 and ridge 94 help to prevent the plunger 80 from being pushed into the nozzle assembly 10 before the piston 72 engages post 92. When sufficient pressure is applied to post 92 by piston 72, the prongs 82 will disengage from groove 98 to allow the plunger 80 to move distally so that prongs 82 and lips 92 engage lead portion 88. Groove 98 also preferably includes a sloped proximal edge 99 which is provided to facilitate manufacturing. Sloped proximal edge 99 is preferably sloped at an angle of θ which is about 45° relative to the longitudinal axis X—X, but angle θ may range from about 0° to 90°.

Figure 20:
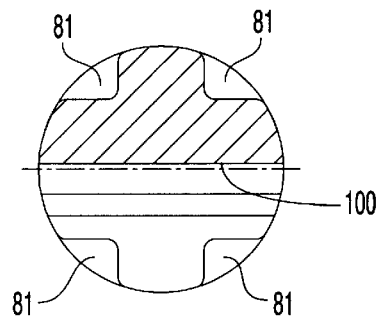
FIG. 20 is a cross-sectional view of the plunger at area 20—20 as shown in FIG. 17.

As shown in FIGS. 17 and 20, plunger 80 of the second embodiment is frangible. It is known to use a frangible piston, as taught by U.S. patent application Ser. No. 5,643,211, which is incorporated herein by reference. Plunger 80 has a first driving member 110 and a second driving member 120. As shown, these members have a generally cylindrical shape with specially shaped base 112, 122 and end portions 114, 124. While a plunger having a D-shaped end and base portions can be used, it is preferred to use a modified D-shape wherein portions of the arcuate part of the D 81 have been removed, as shown in FIG. 20. These driving members 110, 120 are connected together in a spaced apart relationship across a predetermined gap G by a frangible connection or bridge 100.

As shown in FIG. 17, the preferred frangible bridge 100 is a relatively thin, overlapping and connecting portion of the first and second driving members 110, 120. It is preferred that the height of the frangible bridge be minimal to provide a localized shear zone. The frangible portion 100 may be disposed adjacent both straight sides of end portions 114, 124 of the first and second driving members 110, 120. A leading or distal edge 111 of frangible portion 100 is preferably shaped as a sharp corner. This sharp corner provides stress concentration for assisting in shearing the frangible portion when an appropriate load is applied to the second driving member 120. A trailing or proximal edge 121 of frangible portion 100 is preferably rounded, defining a radius. This radius is defined to provide a clean two-part break which allows the second driving member 120 to close the gap G between the first 110 and second 120 driving members.

Further, recesses 123 are defined at the end of the channels which define the frangible portion 100. These recesses are positioned in the base portions 112, 122, adjacent the frangible portion 100, and are configured and dimensioned to accept flash or waste which may break away from the frangible bridge 100 during shearing. Recesses 123 are provided in order to avoid any interference between any flash and the movement of the first and second driving members 110, 120.

Frangible portion 100 is preferably spaced a small distance from longitudinal axis X—X in order to aid in providing a frangible connection which will shear when a sufficient amount of force is applied. Preferably, the plunger 80, including the frangible bridge is made out of a plastic and is configured and dimensioned such that frangible portion 100 can withstand a force "p" for moving or withdrawing the plunger to draw liquid medication into chamber 40 without breaking. Typically, an acrylic polymer will provide the strength necessary to withstand loading or medication filling procedures, but is also sufficiently brittle to break when the firing force is applied. The present frangible portion 100 is designed to shear when force "P," which is greater than force "p" is applied.

Alternatively, the frangible plunger 80 can be used with a prefilled chamber 40, thereby eliminating the need for moving the plunger 80 longitudinally to draw liquid medication into chamber 40 or to expel excess liquid or bubbles therefrom.

The leading end of the first driving member 110 includes the seal 86, such as an O-ring or the like, preferably formed around its outer periphery to provide a seal with the inner wall of the chamber 40. The plunger 80 itself can be a seal. Other seals or seal members can be included in the trailing end of the second driving member 120 if desired to provide a better seal to prevent leakage of fluid for the chamber by minimizing the entry of air into the chamber from around the first and second driving members 110, 120 and by preventing air from entering the orifice 42 due to liquid exiting the chamber around the driving members.

As part of the filling operation, the plunger 80 is pushed into the chamber 40, in the distal direction to purge air from the internal chamber, as shown in FIG. 21. As the plunger 80 is pulled in the proximal direction, a partial vacuum is established inside the chamber and liquid medication is drawn into the chamber 40 through the orifice 42.

It will be noted that the frangible connection is dimensioned and configured such that pushing or pulling action requiring force "p" normally affiliated with withdrawal and slow ejection of air or medication before injection does not break the bridge 100. Upon an application of a relatively large injection force "P" on the ram, which may be significantly larger than the force "p", the ram transmits this force "P" to the second driving member 120 and breaks the frangible portion 100. This allows the second driving member 120 to close the gap G and transmit force to the first driving member 110 so that the respective base 112, 122 and end 114, 124 portions meet to eject medication out of the chamber 40. Specifically, the end portion 114 of the second driving member 120 contacts the base portion 112 of the first driving member 110 while the base portion 122 of the second driving member 120 contacts the end portion 124 of the first driving member 110 for urging the first driving member 110 towards the chamber orifice 42 to expel fluid therefrom.

FIG. 22A shows the position of the plunger 80 after the injection is completed and all the medication has been ejected. In this position, the frangible connection 100 has been broken so that the first 110 and second 120 driving members are in contact and the plunger 80 is positioned in the distal end of the chamber 40.

Finally, FIG. 22B shows the position of the plunger 80 after the injection is completed and the nozzle assembly 10 has been rotated or unlocked from the injector. The nozzle assembly has been rotated so that rib segments 16 are free of the injector 30 and can be removed. At this point, as the nozzle assembly 10 is withdrawn or pulled back from the injector 30, the piston 72 and second driving member 120 move proximally within the chamber 40 until the outwardly curved prongs 82 engage the outwardly tapered portion 96 of the nozzle assembly 10. When this engagement occurs within the tapered portion 96, the piston 72 is freed from the prongs 82 and the nozzle assembly 10 may be completely removed from the injector 30. Thus, the first 110 and second 120 driving members remain inside the nozzle assembly and are easily removed from the injector 30 and the nozzle assembly 10 then may not be reused and must be discarded. This prevents unwanted re-use of the nozzle assembly.

In a normal operation of the injector, piston 72 of the injection device operatively connected to an energy source 32 imparts sudden force or impact "P" to the second driving member 120, enough to drive the second member 120 into the first member 110. This action is sufficient to drive the liquid contained in chamber 40 outward through orifice 42 as a peak jet stream pressure for example in excess of 5,000 psi out of the orifice 42. This sudden force "P" is capable of breaking the frangible bridge 100 before the injection begins. Specifically, the force "P" applied to the second driving member 120 is transmitted to the first driving member 110 through the bridge 100. Initially, the frictional force in the seal 86 generates enough friction to momentarily prevent the plunger 80 from moving. Once this frictional force is overcome, the plunger 80 starts to move and imparts pressure to the medication in the chamber 40. This creates resistance or back pressure on the first driving member 110. When the difference between the resistance force imparted to first driving member 110 by the fluid and the force imparted by the second driving member 120 toward the first driving member 110 reaches a predetermined level, the bridge 100 breaks and the second driving member 120 rams into the first driving member 110.

Alternatively, frangible bridge 100 may be broken by an intermediate force larger than the force "p," before the relatively large injection force "P" is applied to piston 72. Such an intermediate force can be generated for example by a pressure exerted on the liquid contained in chamber 40 through orifice 42 or by other triggering mechanism.

The gap "G" plays an important role in creating a preferred pressure spike necessary to pierce through the patient's skin. Changing the gap G will change the initial force imparted on the first driving member 110. The peak pressure thus can be varied with the gap G. It can also vary depending upon the viscosity of the medication, the desired injection penetration depth, and other parameters which may affect the initial injection pressure output. One of ordinary skill in the art can determine by routine experimentation the optimum gap for any frangible plunger that is to be used with a particular medication. Advantageously, frangible plunger 80 or nozzle assembly 10 or both can be manufactured with different colors, wherein each color denotes a predetermined width of gap G. This color coding scheme will assist the user in choosing a proper nozzle assembly 10 for a specific application. In addition, the amount of force to break the bridge 100 can be adjusted by changing the dimension of the bridge 100.

It will be understood that the frangible plunger according to the present invention can also be used with syringes having hypodermic needles where the frangible bridge breaks either before the injection begins or after the completion of the injection. It will also be understood that a plunger with the outwardly curved prongs may be utilized without a frangible portion.

While various features of the present invention were described above, it is understood that the various features of the present invention can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly to be defined as set forth in the appended claims.

What is claimed is:

1. An injector comprising:
   an injector body;
   a nozzle assembly comprising a tubular body having a tip ends, a tail end and an internal chamber defined therebetween, said tip end for positioning against an injection site, said internal chamber configured and dimensioned for holding a medicament and defining an orifice at the tip end for expelling the medicament therefrom;
   connecting means disposed about the circumference of the nozzle assembly tubular body for engaging the injector body; and
   means for locking the nozzle assembly tubular body onto the injector body, the locking means comprising at least one recess in the injector body, and at least one protrusion positioned on an external surface of the nozzle assembly tubular body and configured for engagement with the recess;
   wherein the injector body comprises a retaining element having the at least one recess for engagement by the protrusion, said retaining element having a first end for accepting the nozzle assembly, and a second end opposite the first end forming a wall having an opening and the retaining element comprises a cylindrical ring having an internal diameter at least equal to or greater than the external diameter of the nozzle assembly tubular body and the retaining element is retained within the interior of the injector.

2. The injector of claim 1, wherein the protrusion extends longitudinally from the tail end of the tubular body and the recess is located in the wall of the retaining element and is configured and dimensioned so that the user receives positive tactile feedback when the protrusion enters the recess.

3. The injector of claim 1, wherein the connecting means is substantially centrally located on the tubular body and the protrusion is positioned between the connecting means and the tail end.

4. The injector of claim 3, wherein the connecting means comprises a plurality of teeth which at least partially surround the circumference of the tubular body.

5. The injector of claim 4, wherein the injector body includes a plurality of grooves for mating with the teeth of the nozzle assembly.

6. The injector of claim 5, wherein the teeth are in the form of a partial helix and define rib segments.

7. The injector of claim 6, wherein the rib segments are positioned at a canted angle ranging from about 0° to 7° and have a pitch ranging from about 0.04 to 0.2 inches per thread.

8. The injector of claim 6, wherein at least one of the rib segments is wider than the other rib segments and a corresponding groove in the injector body is sized to mate with the wider rib segment.

9. The injector of claim 6, wherein at least one of the rib segments extends around about one-half the circumference of the tubular body and is configured to interfere with a portion of the injector body.

10. The injector of claim 2, wherein the tubular body further comprises at least one slot located adjacent the protrusion and extending partially transversely in the vicinity of the tail end, said slot allowing for the depression of the protrusion as the nozzle assembly is rotated before the protrusion enters the recess.

11. The injector of claim 2, wherein the tubular body is in a locked position when the protrusion is positioned in the recess.

12. The injector of claim 7 which further comprises indicating means for aligning the tubular body locking means with the injector body.

13. The injector of claim 1, wherein the recess comprises an L-shaped slot having a first and second elongated opening for accepting the protrusion of the nozzle assembly.

14. The injector of claim 13, wherein the first opening of the L-shaped slot extends axially from the first end of the retaining element partially along the length of the retaining element and the second opening of the L-shaped slot extends helically and partially around the circumference of the retaining element from the first opening of the L-shaped slot.

15. The injector of claim 14, wherein the second opening of the L-shaped slot includes a detent for receiving the protrusion of the nozzle assembly, said detent configured and dimensioned so that the user receives positive tactile feedback when the protrusion enters the detent.

16. The injector of claim 15, wherein the tubular body is in a locked position when the protrusion is positioned in the detent.

17. The injector of claim 15, wherein the connecting means are teeth in the form of a partial helix positioned to partially surround the circumference of the tubular body and the second opening is positioned at an angle which is substantially equal to the helical angle of the teeth so that when the nozzle assembly is inserted into and turned in the retaining element, the protrusion travels axially at the same rate as the teeth.

18. The injector of claim 17, wherein the second opening of the L-shaped slot is configured and dimensioned such that when the tubular body is rotated within the retaining element, an interference fit initially occurs between the protrusion and the retaining element such that a resistance is encountered by the user, followed by a decreased resistance as the protrusion engages an enlarged portion of the end of the second opening.

19. The injector of claim 18, wherein the indicating means includes a first marking on the tubular body, a second marking on the exterior of the injector body, and a third marking on the tubular body, said first marking for alignment with the second marking when the tubular body is inserted longitudinally into the injector body, and said third marking for alignment with the second marking after the tubular body has been inserted longitudinally and rotated into a locked position.

20. An injector comprising:

an injector body;

a nozzle assembly comprising a tubular body having a tip end, a tail end and an internal chamber defined therebetween, said tip end for positioning against an injection site, and said internal chamber configured and dimensioned for holding a medicament and defining an orifice at the tip end for expelling the medicament therefrom;

connecting means disposed about the circumference of the nozzle assembly tubular body for engaging the injector body; and indicator means comprising markings operatively associated with the nozzle assembly tubular body and the injector body for indicating that the nozzle assembly tubular body is properly aligned with the injector body, said markings including a first marking on the nozzle assembly tubular body, a second marking on the exterior of the injector body, and a third marking on the nozzle assembly tubular body, said first marking for alignment with the second marking when the nozzle assembly tubular body is inserted longitudinally into the injector body and said third marking for alignment with the second marking after the nozzle assembly tubular body has been inserted longitudinally and rotated into a final position.

21. An injector comprising:

an injector body;

a nozzle assembly comprising a tubular body having a tip end, a tail end and an internal chamber defined therebetween, said tip end for positioning against an injection site, and said internal chamber configured and dimensioned for holding a medicament and defining an orifice at the tip end for expelling the medicament therefrom;

connecting means disposed about the circumference of the tubular body for engaging the injector body, said connecting means comprising a plurality of teeth which at least partially surround the circumference of the nozzle assembly tubular body to define rib segments, with at least one rib segment being configured differently than the other rib segments and the tubular body being operatively associated with the at least one differently configured rib segment for insuring proper positioning of the nozzle assembly tubular body in the injector body; and means for locking the nozzle assembly tubular body onto the injector, said locking means comprising at least one non-annular recess in the injector body, and at least one protrusion positioned on an external surface of the nozzle assembly tubular body and configured for engagement with the recess.

22. The nozzle assembly of claim 21, wherein the differently configured rib segment has a wider cross-section that the other rib segments and a groove provided in the injector is configured and dimensioned for receiving the wider rib segment.

23. The nozzle assembly of claim 21, wherein the differently configured rib segment is longer than the other rib segments and a portion of the injector is configured and dimensioned to interfere with the longer rib segment to deter improper insertion of the nozzle assembly into the injector.

* * * * *

UNITED STATES PATENT AND TRADEMARK OFFICE
CERTIFICATE OF CORRECTION

PATENT NO. : 5875976

DATED : 03/02/99

INVENTOR(S) :. Sheldon Nelson

It is certified that error appears in the above-identified patent and that said Letters Patent is hereby corrected as shown below:

Delete drawing sheets 1-4, and 6, substitute therefore the Drawing Sheets, consisting of Figs 1-11 and 16, as shown on the attached pages.

Column 8 line 17, change "rim 70" to --rim 70' --.
Column 9, line 57, change "first opening 72" to --first opening 72' –
Column 10, line 4, change "first opening 72' to --first opening 72' --

Signed and Sealed this

Tenth Day of August, 1999

Q. TODD DICKINSON

*Attest:*

*Attesting Officer*

Acting Commissioner of Patents and Trademarks